United States Patent
Wu et al.

(10) Patent No.: US 6,900,210 B2
(45) Date of Patent: May 31, 2005

(54) PYRIDINYL, PYRIMIDINYL AND PYRAZINYL AMIDES AS POTASSIUM CHANNEL OPENERS

(75) Inventors: Yong-Jin Wu, Madison, CT (US); Li-Qiang Sun, Glastonbury, CT (US); Jie Chen, Madison, CT (US); Huan He, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/719,538

(22) Filed: Nov. 21, 2003

(65) Prior Publication Data

US 2004/0102449 A1 May 27, 2004

Related U.S. Application Data

(60) Provisional application No. 60/428,352, filed on Nov. 22, 2002.

(51) Int. Cl.[7] .................. C07D 213/643; C07D 239/34; C07D 241/18; A61K 31/4412; A61K 31/513
(52) U.S. Cl. .................... 514/252.1; 514/274; 514/314; 514/336; 514/351; 544/316; 544/408; 546/175; 546/280.4; 546/281.4; 546/283.4; 546/284.7; 546/300
(58) Field of Search ................................. 544/316, 408; 546/175, 300, 280.4, 281.4, 283.4, 284.7; 514/252.1, 274, 351, 314, 336

(56) References Cited

U.S. PATENT DOCUMENTS

| 4,927,838 A | 5/1990 | Guthrie et al. ............... 514/337 |
| 6,046,239 A | 4/2000 | Lennox et al. ............... 514/563 |
| 6,413,995 B1 | 7/2002 | Hasegawa et al. .......... 514/357 |

FOREIGN PATENT DOCUMENTS

| EP | 810220 A1 | 12/1997 |
| JP | 45-14291 | 5/1970 |
| JP | 2-138159 | 5/1990 |
| WO | WO 98/17639 | * 4/1998 |
| WO | WO 00/07993 | 2/2000 |
| WO | WO 00/42013 | 7/2000 |
| WO | WO 01/10380 | 2/2001 |
| WO | WO 01/10381 | 2/2001 |

OTHER PUBLICATIONS

Layzer, Degenerative Diseases of the Nervous System, Cecil Textbook of Medicine, 20th Edition, vol. 2, pp. 2050–2057, 1996.*

Damasio, Alzheimer's Disease and related dementias, Cecil Textbook of Medicine, 20th Edition, vol. 2, pp. 1992–1996, 1996.*

Wang, S., et al., "KCNQ2 and KCNQ3 Potassium Channel Subunits: Modular Correlates of the M–Channel", *Science*, 282, pp. 1890–1893 (1998).

* cited by examiner

*Primary Examiner*—Deepak Rao
(74) *Attorney, Agent, or Firm*—Aldo A. Algieri

(57) ABSTRACT

The present invention provides novel heterocyclic amides and related derivatives having the general Formula I

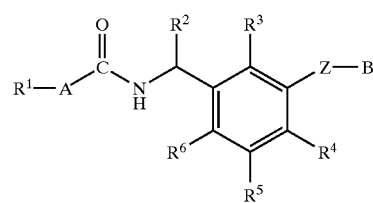

wherein $R^1$, $R^2$, $R^3$, $R^4$, $R^5$, $R^6$, A, B and Z are as defined in the specification, or a nontoxic pharmaceutically acceptable salt, solvate or hydrate thereof which are openers or activators of KCNQ potassium channels. The present invention also provides pharmaceutical compositions comprising said heterocyclic amides and to the method of treatment of disorders sensitive to KCNQ potassium channel opening activity such as migraine or a migraine attack, bipolar disorders, epilepsy, acute and chronic pain and anxiety.

7 Claims, No Drawings

PYRIDINYL, PYRIMIDINYL AND PYRAZINYL AMIDES AS POTASSIUM CHANNEL OPENERS

CROSS-REFERENCE TO RELATED APPLICATIONS

This is a non-provisional application which claims the benefit of U.S. Provisional Application No. 60/428,352 filed Nov. 22, 2002.

FIELD OF THE INVENTION

The present invention is directed to novel heterocyclic amide derivatives which are modulators of KCNQ potassium channels and are therefore useful in treating disorders responsive to the modulation of the potassium channels. The present invention also provides a method of treatment with the novel heterocyclic amide derivatives and to pharmaceutical compositions thereof.

BACKGROUND OF THE INVENTION

Potassium ($K^+$) channels are considered to be the most diverse class of ion channels and have several critical roles in cell function. This has been demonstrated in neurons where $K^+$ channels are responsible, in part, for determining cell excitability by contributing to membrane repolarization following depolarization, resting membrane potential, and regulation of neurotransmitter release. The M-current has long been described, by electrophysiology recording methods and by pharmacology, as a dominant conductance in controlling neuronal excitability. Pharmacological activation or suppression of M-currents by small molecules could have profound effects in controlling neuronal excitability. Recently, Wang et al., Science, 282:1890–1893, (1998) reported that co-assembly of the KCNQ2 and KCNQ3 potassium channels underlies the native M-current in neurons.

Activation or opening of the KCNQ channel(s), particularly the KCNQ2 or KCNQ2/3 channel(s), mutated or wild type, may prove to be beneficial in increasing hyperpolarization of neurons, thereby resulting in protection from abnormal synchronous firing during a migraine attack. The present invention provides a solution to the problem of abnormal synchronous firing of neurons related to migraine headache by demonstrating that modulators, preferably openers, of KCNQ potassium channels increases hyperpolarization of neurons which protects against abnormal synchronous neuron firing involved in migraine attacks.

Although the symptom pattern varies among migraine sufferers, the severity of migraine pain justifies a need for vigorous, yet safe and effective, treatments and therapies for the great majority of cases. Needed in the art are agents that can be used to combat and relieve migraine (and diseases similar to and mechanistically related to migraine), and even prevent the recurrence of migraine. Also needed are anti-migraine agents which are effective in the treatment of acute migraine, as well as in the prodrome phase of a migraine attack. Thus, a clear goal in the art is to discover new, safe, nontoxic and effective anti-migraine compounds for use as drugs, and in anti-migraine compositions and treatments.

Because migraine afflicts a large percentage of the population, there is a need to discover compounds and agents that are useful in therapeutics and treatments, and as components of pharmaceutical compositions, for reducing, ameliorating, or alleviating the pain and discomfort of migraine headache and other symptoms of migraine. The present invention satisfies such a need by providing compounds that function as openers of the KCNQ family of potassium channel proteins to serve as anti-migraine agents or drugs and to comprise compositions to treat migraine, as described herein.

A broad range of cinnamide compounds are known and new compounds continue to be reported with a broad range of utility. Some of these compounds can be found in the disclosures of WO 00/07993 published Feb. 17, 2000, EP 810220A1, published Dec. 3, 1997, U.S. Pat. No. 4,927,838 issued May 22, 1990 to Guthrie, et al., U.S. Pat. No. 6,046,239 issued Apr. 4, 2000 to Lennox, et al., WO 00.42013, published Jul. 20, 2000, WO 01/10381 published Feb. 15, 2001, WO 01/10380 published Feb. 15, 2001, JP45-14291 published May 21, 1970, and JP2-138159 published May 28, 1990. The compounds described in these patents are distinct from those of the present invention.

SUMMARY OF THE INVENTION

The present invention provides novel heterocyclic amides and related derivatives having the general Formula I

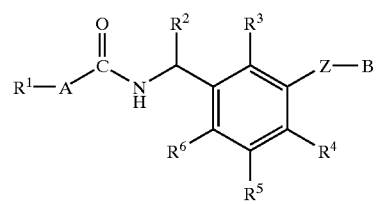

wherein $R^1$, $R^2$, $R^3$, $R^4$, $R^5$, $R^6$, A, B and Z are as defined below, or a nontoxic pharmaceutically acceptable salt, solvate or hydrate thereof which are openers or activators of KCNQ potassium channels. The present invention also provides pharmaceutical compositions comprising said heterocyclic amides and to the method of treatment of disorders sensitive to KCNQ potassium channel opening activity such as migraine or a migraine attack, bipolar disorders, epilepsy, acute and chronic pain and anxiety.

DETAILED DESCRIPTION OF THE INVENTION

The present invention provides novel heterocyclic amides and related derivatives which are modulators of the KCNQ potassium channels and which have the general Formula I or a pharmaceutically acceptable salt thereof

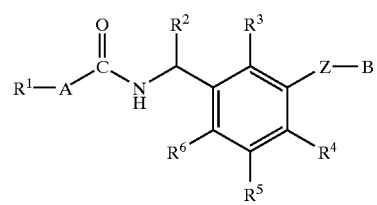

wherein $R^1$ is selected from the group consisting of pyridinyl, 3-quinolinyl, thienyl, furanyl, $C_{3-6}$ cycloalkyl and phenyl optionally substituted with substituent independently selected from the group consisting of halogen, $C_{1-4}$ alkyl, $C_{1-4}$ alkoxy, trifluoromethyl, trifluoromethoxy and nitro; A is —CH=CH— or —$(CH_2)_n$—; $R^2$ is $C_{1-4}$ alkyl, $CF_3$ or hydroxymethyl; $R^3$, $R^4$, $R^5$ and $R^6$ each are independently hydrogen or fluoro; Z is oxygen or —$NR^7(CH_2)_m$—; n is an integer of 0, 1, 2 or 3; m is an integer of 0 or 1; $R^7$ is hydrogen or $C_{1-4}$ alkyl; and B is pyridinyl, pyrimidinyl or pyrazinyl optionally substituted with a subsituent selected from the group consisting of $C_{1-4}$ alkyl, halogen, $C_{1-4}$ alkoxy and trifluoromethyl.

The present invention also provides a method for the treatment or alleviation of disorders associated with KCNQ potassium channel polypeptides and, in particular, human KCNQ potassium channel polypeptides in a mammal in need thereof which comprises administering together with a conventional adjuvant, carrier or diluent a therapeutically effective amount of a compound of Formula I or a pharmaceutically acceptable salt thereof. Preferably, the compounds of Formula I are useful in the treatment of migraine or a migraine attack, cluster headaches, bipolar disorder, convulsions, mania, acute mania, epilepsy, anxiety, depression, schizophrenia, functional bowel disorders, stroke, traumatic brain injury, multiple sclerosis, neurodegenerative disorders or alleviating pain such as musculoskeletal pain, post operative pain, surgical pain, inflammatory pain, neuropathic pain such as diabetic neuropathy and pain associated with cancer and fibromyalgia.

The term "pain" as used herein and in the claims means all types of acute and chronic pain, such as neuropathic pain, post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis and the term also is intended to include nociceptive pain or nociception.

The term "$C_{1-4}$ alkyl" as used herein and in the claims means straight or branched chain alkyl groups such as methyl, ethyl, propyl, isopropyl, butyl, isobutyl, and tert-butyl. The term "$C_{1-4}$ alkoxy" as used herein and in the claims means an oxygen substituted with straight or branched chain alkyl groups and includes groups such as methoxy, ethoxy, propoxy, isopropoxy, butoxy, isobutoxy, and tert-butoxy. The term "halogen" as used herein and in the claims is intended to include bromine, chlorine, iodine and fluorine.

As the compounds of the present invention contain a substituted carbon-carbon double bond as part of the structure, the compounds of the invention exist in either of two geometric isomeric forms, namely as cis or trans isomers. Preferred are the trans isomers in which the group $R^1$ is —CH═CH— and the amide group, C(O)NH, are trans to each other. As the compounds of the present invention possess an asymmetric carbon atom, such as the carbon adjacent to the amide nitrogen and to which the phenyl is attached, the present invention includes the racemate as well as the individual enantiomeric forms of the compounds of Formula I as described herein and in the claims. Preferred embodiments of compounds of Formula I include the racemate, a single enantiomer, and in certain instances a single enantiomer wherein the carbon adjacent to the amide nitrogen and to which the phenyl is attached has the (S) stereochemistry. Mixtures of isomers of the compounds of Formula I or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns, according to procedures described herein.

Certain of the compounds of the present invention can exist in unsolvated forms as well as solvated forms including hydrated forms such as monohydrate, dihydrate, trihydrate, hemihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the method that is sufficient to show a meaningful patient benefit, i.e., amelioration or healing of conditions which respond to modulation of the KCNQ potassium channels. When applied to an individual active ingredient, administered alone, the term refers to that ingredient alone. When applied to a combination, the term refers to combined amounts of the active ingredients that result in the therapeutic effect, whether administered in combination, serially or simultaneously. The term "KCNQ" as used herein and in the claims means the family of KCNQ2, KCNQ3, KCNQ4, and KCNQ5 potassium channel polypeptides as well as heteromultimers of different individual family members which include but are not limited to KCNQ2/3, KCNQ2/5 and KCNQ3/5. The terms "treat, treating, treatment" as used herein and in the claims means preventing, alleviating or ameliorating diseases and/or symptoms associated with dysfunction of cellular membrane polarization and conductance of human KCNQ2, KCNQ3, KCNQ4, and KCNQ5 potassium channel polypeptides and, in particular, migraine and/or symptoms that precede a full-blown migraine attack, neuropathic pain, mania and anxiety.

The general procedures used to synthesize intermediates and the compounds of Formula I are described in Reaction Schemes 1–4 and are illustrated in the preparations and examples. Reasonable variations of the described procedures, which would be evident to one skilled in the art, are intended to be within the scope of the present invention.

Reaction Scheme 1

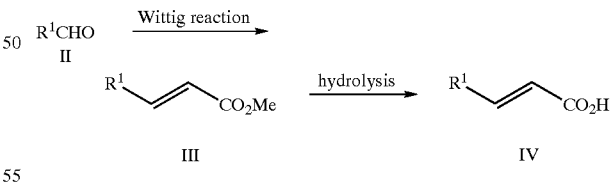

Reaction Scheme 1 depicts the preparation of cinnamic acid derivatives useful as intermediates in the synthesis of compounds of Formula I. Step 1 of Reaction Scheme 1 depicts the Wittig reaction of an appropriate aldehyde of Formula II with an appropriate Wittig reagent to provide the methyl ester of Formula III. Hydrolysis of the methyl ester of Formula III can be accomplished using an appropriate base such as sodium hydroxide or lithium hydroxide in an appropriate solvent followed by acidification with an appropriate acid such as 1N hydrochloric acid to provide the cinnamic acid of Formula IV.

Reaction Scheme 1

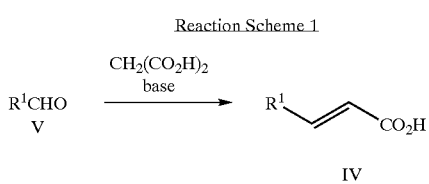

Reaction Scheme 2 depicts an alternative preparation of an cinnamic acid derivative of Formula IV which can then be used to prepare compounds within general Formula I.

Reaction Scheme 3

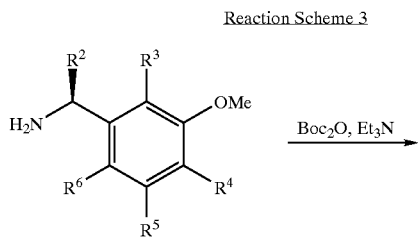

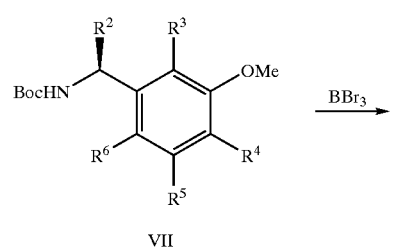

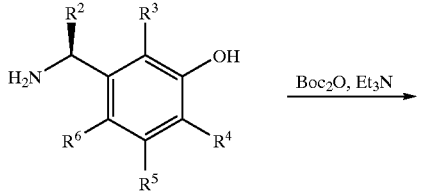

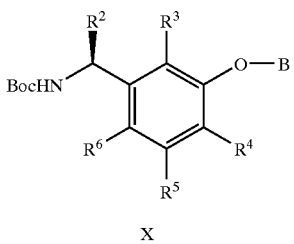

Reaction Scheme 3 depicts a general method useful for the preparation of amines of Formula X which are useful intermediates for the preparation of compounds of Formula I. Compound of Formula VI is converted to compound of Formula VII by treatment with di-t-butyl-di-carbonate and triethylamine. Exposure of compound of Formula VII with boron tribromide afforded compound of Formula VIII, and the amine group was protected to give compound of Formula IX. Compound of Formula IX was treated with B-Halo in the presence of copper iodide under basic conditions to furnish compound of Formula X.

Reaction Scheme 4

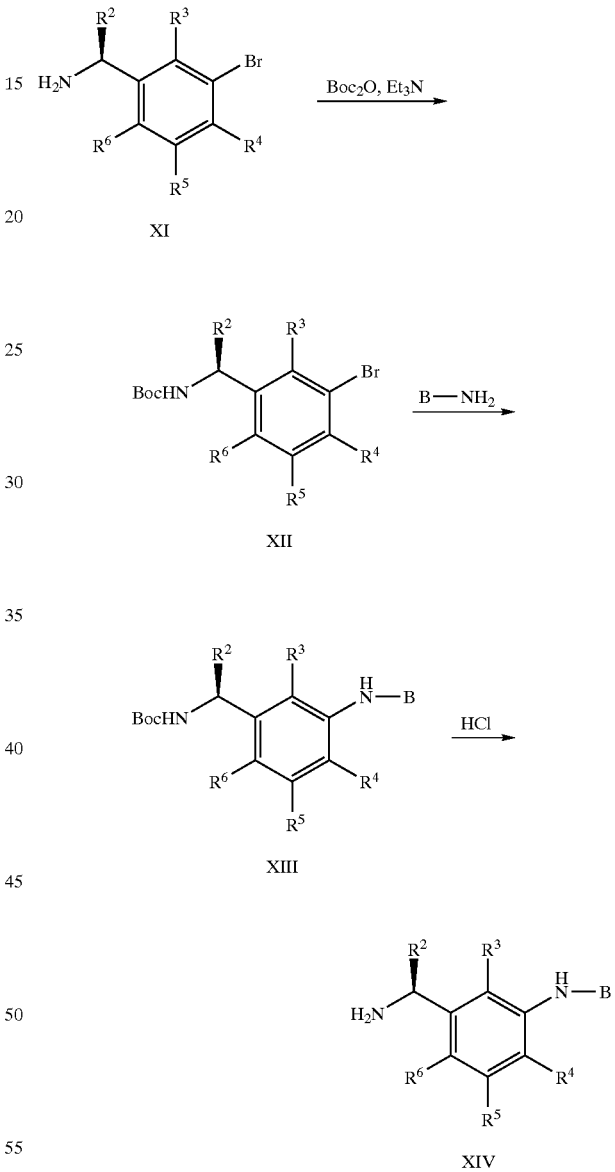

Reaction Scheme 4 depicts a general method useful for the preparation of amines of Formula XIV which are useful intermediates for the preparation of compounds of Formula I. Compound of Formula XI can be converted to compound of Formula XII by treatment with di-t-butyl-di-carbonate and triethylamine. Compound of Formula XII underwent the palladium-catalyzed amination to furnish compound of Formula XIII, which was hydrolyzed under acidic conditions such as 1N hydrochloric acid to afford compound of Formula XIV.

Reaction Scheme 5

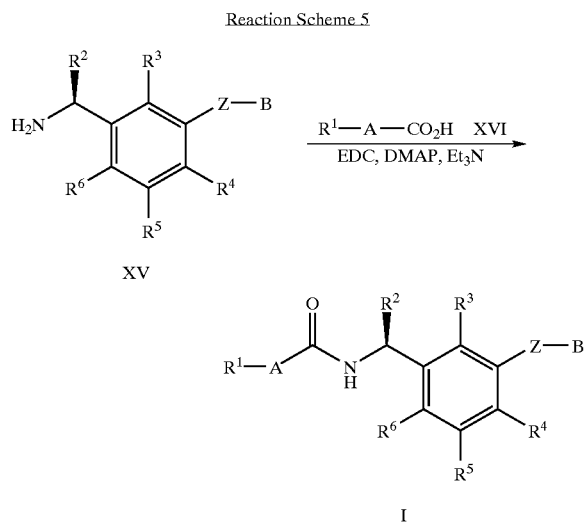

Reaction Scheme 5 depicts the preparation of compounds of general Formula I from the acid of general Formula XVI and amine of general Formula XV. The coupling of the acid, XVI, and amine, XV carried out by methodology well known in the art for the conversion of an acid and an amine to form an amide. Useful reactive derivatives of the acid of Formula XVI include, but are not limited to, activated esters, reactive mixed anhydrides, and acid halides (such as the acid chloride, prepared e.g. with thionyl chloride or oxalyl chloride). A preferred method is to condense the acid of Formula XVI with the amine of Formula XV in the presence of an appropriate condensing agent, for example, 1-(3-dimethylaminopropyl)-3-ethylcarbodiimide (EDC) or dicyclohexylcarbodiimide (DCC), and a basic tertiary amine, such as 4-dimethylaminopyridine (DMAP), in an inert solvent such as dichloromethane. The more preferred method is to couple the acid of Formula XVI with the amine of Formula XV in the presence of 1-(3-dimethylaminopropyl)-3-ethylcarbodiimide, hydrochloride (EDC) in the presence of 4-dimethylaminopyridine (DMAP), triethylamine ($Et_3N$), in dichloromethane.

In one embodiment, the present invention includes compounds of Formula I or a pharmaceutically acceptable salt thereof

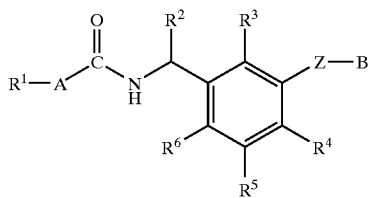

I wherein $R^1$ is selected from the group consisting of pyridinyl, 3-quinolinyl, thienyl, furanyl, $C_{3-6}$ cycloalkyl and phenyl optionally substituted with substituent independently selected from the group consisting of halogen, $C_{1-4}$ alkyl, $C_{1-4}$ alkoxy, trifluoromethyl, trifluoromethoxy and nitro; A is —CH=CH— or —$(CH_2)_n$—; $R^2$ is $C_{1-4}$ alkyl, $CF_3$ or hydroxymethyl; $R^3$, $R^4$, $R^5$ and $R^6$ each are independently hydrogen or fluoro; Z is oxygen or —$NR^7(CH_2)_m$—; n is an integer of 0, 1, 2 or 3; m is an integer of 0 or 1; $R^7$ is hydrogen or $C_{1-4}$ alkyl; and B is pyridinyl, pyrimidinyl or pyrazinyl optionally substituted with a subsituent selected from the group consisting of $C_{1-4}$ alkyl, halogen, $C_{1-4}$ alkoxy and trifluoromethyl.

In a preferred embodiment, the invention includes compounds of Formula Ia or a pharmaceutically acceptable salt thereof

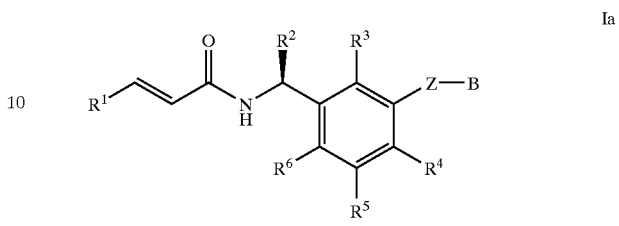

Ia wherein $R^1$ is selected from the group consisting of pyridinyl, 3-quinolinyl, thienyl, furanyl, $C_{3-6}$ cycloalkyl and phenyl optionally substituted with substituent independently selected from the group consisting of halogen, $C_{1-4}$ alkyl, $C_{1-4}$ alkoxy, trifluoromethyl, trifluoromethoxy and nitro; A is —CH=CH— or —$(CH_2)_n$—; $R^2$ is methyl; $R^3$, $R^4$, $R^5$ and $R^6$ each are independently hydrogen or fluoro; Z is oxygen or —$NR^7(CH_2)_m$—; n is an integer of 0, 1, 2 or 3; m is an integer of 0 or 1; $R^7$ is hydrogen or $C_{1-4}$ alkyl; and B is pyridinyl, pyrimidinyl or pyrazinyl optionally substituted with a subsituent selected from the group consisting of $C_{1-4}$ alkyl, halogen, $C_{1-4}$ alkoxy and trifluoromethyl.

In another preferred embodiment, the invention includes compounds of Formula Ia or a pharmaceutically acceptable salt thereof

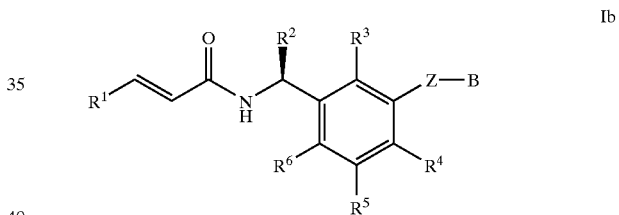

Ib wherein $R^1$ is selected from the group consisting of pyridinyl, 3-quinolinyl, thienyl, furanyl, $C_{3-6}$ cycloalkyl and phenyl optionally substituted with substituent independently selected from the group consisting of halogen, $C_{1-4}$ alkyl, $C_{1-4}$ alkoxy, trifluoromethyl, trifluoromethoxy and nitro; A is —CH=CH— or —$(CH_2)_n$—; $R^2$ is hydroxymethyl; $R^3$, $R^4$, $R^5$ and $R^6$ each are independently hydrogen or fluoro; Z is oxygen or —$NR^7(CH_2)_m$—; n is an integer of 0, 1, 2 or 3; m is an integer of 0 or 1; $R^7$ is hydrogen or $C_{1-4}$ alkyl; and B is pyridinyl, pyrimidinyl or pyrazinyl optionally substituted with a subsituent selected from the group consisting of $C_{1-4}$ alkyl, halogen, $C_{1-4}$ alkoxy and trifluoromethyl.

Preferred compounds for use in the method of the present invention include the compounds of Formula I listed below:
 (S)-3-(2-fluoro-phenyl)-N-{1-[3-(pyridin-2-yloxy)-phenyl]-ethyl}-acrylamide;
 (S)-3-(3-fluoro-phenyl)-N-{1-[3-(pyridin-2-yloxy)-phenyl]-ethyl}-acrylamide;
 (S)-3-(4-fluoro-phenyl)-N-{1-[3-(pyridin-2-yloxy)-phenyl]-ethyl}-acrylamide;
 (S)-3-(2,3-difluoro-phenyl)-N-{1-[3-(pyridin-2-yloxy)-phenyl]-ethyl}-acrylamide;
 (S)-3-(2,4-difluoro-phenyl)-N-{1-[3-(pyridin-2-yloxy)-phenyl]-ethyl}-acrylamide;
 (S)-3-(2,5-difluoro-phenyl)-N-{1-[3-(pyridin-2-yloxy)-phenyl]-ethyl}-acrylamide;

(S)-3-(2,6-difluoro-phenyl)-N-{1-[3-(pyridin-2-yloxy)-phenyl]-ethyl}-acrylamide;
(S)-3-(3,4-difluoro-phenyl)-N-{1-[3-(pyridin-2-yloxy)-phenyl]-ethyl}-acrylamide;
(S)-3-(3,5-difluoro-phenyl)-N-{1-[3-(pyridin-2-yloxy)-phenyl]-ethyl}-acrylamide;
(S)-3-(2-fluoro-phenyl)-N-{1-[3-(pyridin-3-yloxy)-phenyl]-ethyl}-acrylamide;
(S)-3-(3-fluoro-phenyl)-N-{1-[3-(pyridin-3-yloxy)-phenyl]-ethyl}-acrylamide;
(S)-3-(4-fluoro-phenyl)-N-{1-[3-(pyridin-3-yloxy)-phenyl]-ethyl}-acrylamide;
(S)-3-(2,3-difluoro-phenyl)-N-{1-[3-(pyridin-3-yloxy)-phenyl]-ethyl}-acrylamide
(S)-3-(2,4-difluoro-phenyl)-N-{1-[3-(pyridin-3-yloxy)-phenyl]-ethyl}-acrylamide;
(S)-3-(2,5-difluoro-phenyl)-N-{1-[3-(pyridin-3-yloxy)-phenyl]-ethyl}-acrylamide;
(S)-3-(3,4-difluoro-phenyl)-N-{1-[3-(pyridin-3-yloxy)-phenyl]-ethyl}-acrylamide;
(S)-3-(4-fluoro-phenyl)-N-{1-[3-(6-methyl-pyridin-3-yloxy)-phenyl]-ethyl}-acrylamide;
(S)-3-(2,4-difluoro-phenyl)-N-{1-[3-(6-methyl-pyridin-3-yloxy)-phenyl]-ethyl}-acrylamide;
(S)-3-(2,5-difluoro-phenyl)-N-{1-[3-(6-methyl-pyridin-3-yloxy)-phenyl]-ethyl}-acrylamide;
(S)-N-{1-[3-(6-methyl-pyridin-3-yloxy)-phenyl]-ethyl}-3-(2,4,5-trifluorophenyl)-acrylamide;
(S)-3-(2-fluoro-phenyl)-N-{1-[3-(pyridin-4-yloxy)-phenyl]-ethyl}-acrylamide;
(S)-3-(3-fluoro-phenyl)-N-{1-[3-(pyridin-4-yloxy)-phenyl]-ethyl}-acrylamide;
(S)-3-(4-fluoro-phenyl)-N-{1-[3-(pyridin-4-yloxy)-phenyl]-ethyl}-acrylamide;
(S)-3-(2,3-difluoro-phenyl)-N-{1-[3-(pyridin-4-yloxy)-phenyl]-ethyl}-acrylamide;
(s)-3-(2,4-difluoro-phenyl)-N-{1-[3-(pyridin-4-yloxy)-phenyl]-ethyl}-acrylamide;
(S)-3-(2,6-difluoro-phenyl)-N-{1-[3-(pyridin-4-yloxy)-phenyl]-ethyl}-acrylamide;
(S)-3-(2,5-difluoro-phenyl)-N-{1-[3-(pyridin-4-yloxy)-phenyl]-ethyl}-acrylamide;
(S)-3-(3,4-difluoro-phenyl)-N-{1-[3-(pyridin-4-yloxy)-phenyl]-ethyl}-acrylamide;
(S)-3-(3,5-difluoro-phenyl)-N-{1-[3-(pyridin-4-yloxy)-phenyl]-ethyl}-acrylamide;
(S)-3-(2,4-difluoro-phenyl)-N-{1-[3-(pyridin-4-yloxy)-phenyl]-ethyl}-propionamide;
(S)-3-(3,4-difluoro-phenyl)-N-{1-[3-(pyridin-4-yloxy)-phenyl]-ethyl}-propionamide;
(S)-3-(2-fluoro-phenyl)-N-{1-[3-(pyrazin-2-yloxy)-phenyl]-ethyl}-acrylamide;
(S)-3-(3-fluoro-phenyl)-N-{1-[3-(pyrazin-2-yloxy)-phenyl]-ethyl}-acrylamide;
(S)-3-(4-fluoro-phenyl)-N-{1-[3-(pyrazin-2-yloxy)-phenyl]ethyl}-acrylamide;
(S)-3-(2,3-difluoro-phenyl)-N-{1-[3-(pyrazin-2-yloxy)-phenyl]-ethyl}-acrylamide;
(S)-3-(2,4-difluoro-phenyl)-N-{1-[3-(pyrazin-2-yloxy)-phenyl]-ethyl}-acrylamide;
(S)-3-(2,6-difluoro-phenyl)-N-{1-[3-(pyrazin-2-yloxy)-phenyl]-ethyl}-acrylamide;
(S)-3-(3,5-difluoro-phenyl)-N-{1-[3-(pyrazin-2-yloxy)-phenyl]-ethyl}-acrylamide;
(S)-3-(2,3-difluoro-phenyl)-N-{1-[3-(pyrimidin-2-yloxy)-phenyl]-ethyl}-acrylamide;
(S)-3-(2,6-difluoro-phenyl)-N-{1-[3-(pyrimidin-2-yloxy)-phenyl]-ethyl}-acrylamide;
(S)-3-(2-fluoro-phenyl)-N-{1-[3-(pyrimidin-5-yloxy)-phenyl]-ethyl}-acrylamide;
(S)-3-(3-fluoro-phenyl)-N-{1-[3-(pyrimidin-5-yloxy)-phenyl]-ethyl}-acrylamide;
(S)-3-(4-fluoro-phenyl)-N-{1-[3-(pyrimidin-5-yloxy)-phenyl]-ethyl}-acrylamide;
(S)-3-(2,4-difluoro-phenyl)-N-{1-[3-(pyrimidin-5-yloxy)-phenyl]-ethyl}-acrylamide;
(S)-N-[1-(3-benzylamino-phenyl)-ethyl]-3-(2-fluoro-phenyl)-acrylamide;
(S)-N-[1-(3-benzylamino-phenyl)-ethyl]-3-phenyl-acrylamide;
(S)-N-[1-(3-benzylamino-phenyl)-ethyl]-3-(2,4-difluoro-phenyl)-acrylamide; and
(S)-N-[1-(3-benzylamino-phenyl)-ethyl]-3-(2,6-difluoro-phenyl)-acrylamide;
or a pharmaceutically acceptable salt thereof.

Biological Activity
KCNO Patch-Clamp Methods and Results

Potassium ($K^+$) channels are structurally and functionally diverse families of $K^+$-selective channel proteins which are ubiquitous in cells, indicating their central importance in regulating a number of key cell functions [Rudy, B., Neuroscience, 25: 729–749 (1988)]. While widely distributed as a class, $K^+$ channels are differentially distributed as individual members of this class or as families. [Gehlert, D. R., et al., Neuroscience, 52: 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the KCNQ family exemplified by KCNQ2, KCNQ2/3 heteromultimers, and KCNQ5, is regulated by transmembrane voltage and plays a potentially important role in the regulation of neuronal excitability [Biervert, C., et al., Science, 279: 403–406 (1998); Lerche, C. et al., J. Biol. Chem. 275:22395–22400 (2000); Wang, H. et al., Science, 282:1890–1893 (1998)].

An opener of KCNQ channels, such as the KCNQ2 and KCNQ2/3 channel opener retigabine, exerts its cellular effects by increasing the open probability of these channels [Main J., Mol Pharmacol 58(2):253–62 (2000); Wickenden, A. et al., Mol. Pharm. 58:591–600 (2000)]. This increase in the opening of individual KCNQ channels collectively results in the hyperpolarization of cell membranes, particularly in depolarized cells, produced by significant increases in whole-cell KCNQ-mediated conductance.

Whole-cell patch-clamp recordings were made from an HEK 293 stable cell line expressing mKCNQ2 channels, maintained in culture for 1–2 days. Patch pipettes had initial resistances of 2.5–4 MQ. Currents were recorded with an EPC9 amplifier (HEKA, Lambrecht, Germany) controlled with software (Pulse, HEKA) run on a standard lab PC. Series resistance compensation was used during current recording, and set at 80%. The series resistance (R) and cell capacitance (C) were determined electronically by subtracting the capacitive currents at the onset and offset of a 5 mV voltage step. The cancellation of wholecell capacitive transients was virtually complete in all cells. Analog current signals were low-pass filtered at 2.9 kHz using a four-pole Bessel filter −3 dB) and stored on a local network server computer at a sampling rate of 1.5 kHz. All recordings were performed at room temperature (20–22° C.). The pipette solution contained (mM): KCl, 150; CaCl$_2$, 2.5; EGTA, 5; MgCl$_2$, 1; HEPES, 10; pH to 7.3 with KOH, and Osmolality of 290–300 mOsm. The extracellular solution contained (mM): NaCl, 140; KCl, 2.5; CaCl$_2$, 2.5; MgCl$_2$, 1; glucose, 10; HEPES, 10; pH to 7.3 with NaOH, and Osmolality of 305–310 mOsm For analysis of agents effects on mKCNQ2 currents, the raw current records were displayed on the digital oscilloscope of the Pulse software application. Concentration response data were generated by measuring the difference in the steady-state amplitude of current in the presence of compound at the end of a 600 ms voltage-clamp step from a holding potential of −80 mV. The concentration-response data were fitted with Hill-type equations:

$$I = I_{max}/(1 + EC_{50}/[A]^{nH}),$$

where I is the steady-state current at a given concentration of agonist [A]; and $I_{max}$, $EC_{50}$ and nH are parameters estimated from the curve fit. In some cases the concentration-response data were fitted with equations consisting of the sum of two Hill-type components. Current-voltage (IN) relationships for agonist-evoked currents were obtained by performing 600 ms voltage steps (−110 mV to +40 mV) in the absence and presence of agonist. The effect of the representative compounds of Formula I on KCNQ currents is listed in Table 1.

TABLE 1

| Example No. | EC$_{50}$ ($\mu$M) @ −40 mv) | I$_{max}$ (%) |
|---|---|---|
| 9 | 0.0012 | 200 |
| 15 | 0.198 | 812 |
| 25 | 0.001 | 172 |
| 45 | 0.11 | 784 |

Neuropathic Pain Methods and Results
Chung Model of Neuropathic Pain (Chung Surgery and Von Frey Test)

To test agents for activity against peripheral mononeuropathy nerve injury-induced tactile allodynia, male Sprague Dawley rats (wt. 120–160 g) were surgically prepared with unilateral tight ligation of spinal nerves L5 and L6 following the method of Kim and Chung (Kim S. H., Chung J. M. (1992) *Pain, September;* 50(3):355–63). After 3–4 weeks recovery, paw withdrawal to light touch was assessed as described by Chaplan et al. (Chaplan S. R., et al., (1994) *J. Neurosci Methods*, July; 53(1):55–63). In brief, rats are placed in a plastic cage with a wire mesh bottom and allowed to acclimate for 15–30 minutes, until cage exploration and grooming stops. The plantar surface of each hind paw is touched with a series of von Frey hairs with varying stiffness requiring a known force to buckle to determine the nociceptive threshold. Adult male Sprague Dawley rats (avg. wt. 340 g) were tested in the present study. After acclimation, baseline von Frey thresholds were assessed for the injured hindpaw at −15 min. All test compounds were delivered at 0 min by the intravenous (i.v.) route in a volume of 0.5–2 ml/kg. The vehicle for test compounds was 100% PEG-400. For gabapentin the vehicle was deionized H$_2$O. Animals were tested in one of the following 4 treatment conditions: (a) PEG400, (b) gabapentin (Neurontin) 100 mg/kg, (c) test compounds 3 mg/kg and (d) test compounds 10 mg/kg. Following drug administration, von Frey thresholds are measured at 15, 30, 60 and 90 min. Data were analyzed by a 2-way repeated measures analysis of variance followed by Dunnett's test (p<0.05). Experimenters were kept blind to the treatment condition of rats they tested.

Reversal of neuropathic pain behavior may be expressed as a percentage (0–100%) of the maximum possible effect, over and above the vehicle effects. Specifically, drug effects can be described in terms Δ% MPE according to the following equation:

$$\Delta\% \ MPE = \left( \frac{(AUCdrug - AUCvehicle)}{((Time \times Max) - AUCvehicle)} \right) \times 100$$

where:
AUCdrug=area under the curve for von Frey thresholds of the drug-treated group;
AUCvehicle=area under the curve for von Frey thresholds in the vehicle group;
Time=duration of post-drug testing period (90 min); and
Max=maximum von Frey threshold (15 g).

For example, a compound which immediately reversed neuropathic pain behavior to normal levels, such that animals only responded to the highest von Frey filament (15 g), and maintained normal levels through out the post-drug testing period (90 min) would be calculated as Δ% MPE= 100%.

The results for representative compounds of Formula I are provided in Table 2.

TABLE 2

| Example Number | AUC (Δ % MPE)* |
|---|---|
| Gabapentin | 50 (100 mg/kg, i.v.) |
| 15 | 47 (10 mg/kg, i.v.) |

*Δ % MPE = % MPE (Drug AUC) − % MPE (Vehicle AUC)

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of KCNQ potassium channels in a mammal in need thereof, which comprises administering to said mammal a therapeutically effective amount of a compound of Formula I. Preferably, the compounds of Formula I are useful in the treatment of treatment of migraine or a migraine attack, cluster headaches, bipolar disorder, convulsions, mania, acute mania, epilepsy, anxiety, depression, schizophrenia, functional bowel disorders, stroke, traumatic brain injury, multiple sclerosis, neurodegenerative disorders or alleviating pain such as musculoskeletal pain, post operative pain, surgical pain, inflammatory pain, neuropathic pain such as diabetic neuropathy and pain associated with cancer and fibromyalgia.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.01 μg/kg to 10 mg/kg body weight. For parenteral administration, the dose may be in the range of 0.1 μg/kg to 1 mg/kg body weight for intravenous administration. For oral administration, the dose may be in the range about 0.1 μg/kg to 5 mg/kg body weight. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

Unless otherwise stated, solvents and reagents were used directly as obtained from commercial sources, and reactions were performed under a nitrogen atmosphere. Flash chromatography was conducted on Silica gel 60 (0.040–0.063 particle size; EM Science supply). $^1$H NMR spectra were recorded on a Bruker DRX-500f at 500 MHz; a Bruker DPX-300B at 300 MHz; or a Varian Gemini 300 at 300 MHz. The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30) and DMSO-d$_6$ ($\delta_H$ 2.50). Standard acronyms were employed to describe the multiplicity patterns: s (singlet), d (doublet), t (triplet), q (quartet), m (multiplet), b (broad), app (apparent). The coupling constant (j) is in hertz. LC/MS was performed on a Shimadzu LC-10AS liquid chromatograph using a SPD-10AV UV-VIS detector with Mass Spectrometry data determined using a Micromass LC Platform in positive electrospray ionization mode (ESI+). Mass Spectrometry (MS) data was obtained using a standard flow injection technique on a Micromass LC Platform in positive electrospray ionization mode (ESI+) unless otherwise noted. High resolution mass spectrometry (HRMS) data was obtained using a standard flow injection technique on a Finnigan MAT 900 mass spectrometer in electrospray ionization (ESI) mode. The analytical reverse phase HPLC method is as follows unless otherwise noted: Column YMC ODS-A C18 S7 (3.0×50 mm), Start % B 0, Final % B=100, Gradient Time=2 min, Flow rate 5 ml/min. Wavelength 220 nm, Solvent A=10% MeOH-90% H$_2$O-0.1% TFA, Solvent B=90% MeOH-10% H$_2$O-0.1% TFA; and R$_t$ in min. Preparative reverse phase HPLC was performed on a Shimadzu LC-8A automated preparative HPLC system with detector (SPD-10AV UV-VIS) wavelength and solvent systems (A and B) the same as above except where otherwise noted.

The following LCMS conditions were employed for the analysis of the compounds of Examples 1–94 and are as follows:

a) YMC ODS-A C18 S5 4.6×33 mm; 0–100% gradient over 2 min; 5 ml/min flow rate
b) YMC ODS-A 4.6×33 mm; 0–100% gradient over 3 min; 4 ml/min flow rate
c) YMC Xterra C18 S7 3.0×50 mm; 0–100% gradient over 2 min; 5 mL/min flow rate
d) Xterra C18 S5 4.6×50 mm; 0–100% gradient over 2 min; 5 mL/min flow rate

PREPARATIONS OF INTERMEDIATES

Preparation 1

Preparation of (S)-1-[3-(pyridin-3-yloxy)-phenyl-ethylamine

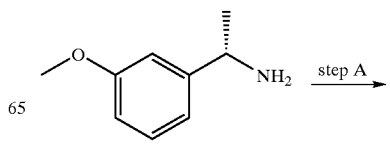

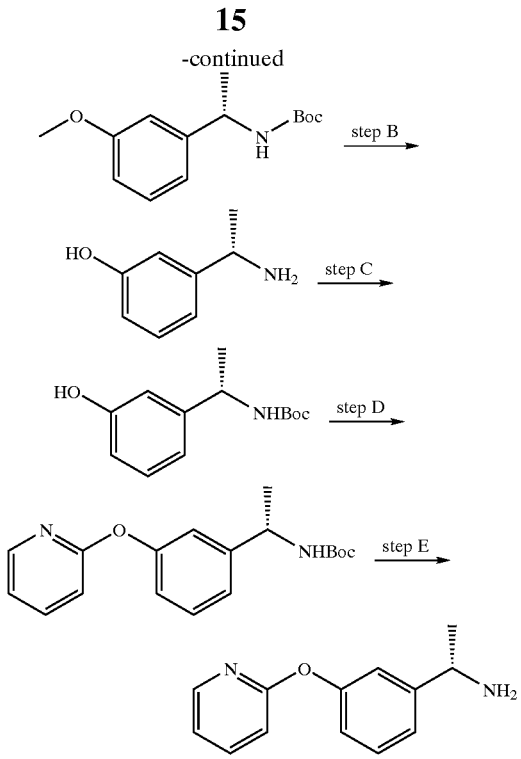

Step A: (S)-[1-(3-Methoxy-phenyl)-ethyl]-carbamic acid tert-butyl ester (S)-1-(3-Methoxy-phenyl)-ethylamine (50.0 g, 331 mmol) and Et₃N (92 mL, 661 mmol) in CH₂Cl₂ (400 mL) was cooled to 0° C. and di-tert-Butyl dicarbonate (86.6 g, 397 mmol) was added. The mixture was warmed to room temperature and stirred for 1 h. then H₂O (100 mL) was added, and the orgahic layer was separated, washed with brine (2×150 mL), dried over anhydrous magnesium sulfate and filtered. The filtrate was concentrated in vacuo to provide the title compound (83 g) as a white solid.

¹H NMR (CDC₃, 300 MHz): δ 1.42 (s, 9H), 1.43 (d, J=7.2 Hz, 3H), 3.80 (s, 3H), 4.76 (bs, 1H), 6.78 (m, 1H), 6.84 (s, 1H), 6.89 (d, J=7.7 Hz, 1H), 7.25 (t,J=7.9 Hz, 1H).

MS: (M+H)⁺ 252

Step B: (S)-3-(1-Amino-ethyl)-phenol (S)-[1-(3-Methoxy-phenyl)-ethyl]-carbamic acid tert-butyl ester (50.2 g, 210 mmol) in CH₂Cl₂ (500 mL) was cooled to −78° C. Boron tribromide (450 mL, 1.0M in CH₂Cl₂) was added slowly and the resulting mixture was warmed to room temperature and stirred for 3 h. The reaction mixture was again cooled to 0° C. and methanol (500 mL) was added slowly. The solvent was removed in vacuo, and the residue was purified by flash column chromatography on silica gel eluting with 5% MeOH in EtOAc to give the title product in quantitative yield.

¹H NMR (CDCl₃,300 MHz): δ 1.30 (d, J=6.6 Hz, 3H), 4.04 (q, J=6.6 Hz, 1H), 6.65 (d, J=7.9 Hz, 1H), 6.79 (s, 1H), 6 80 (d, J=4.6 Hz, 1H), 7.11(t, J=7.9 Hz, 1H).

MS: (M+H)⁺138.

Step C: (S)-[1-(3-Hydroxy-phenyl)-ethyl]-carbamic acid tert-butyl ester

The title compound was prepared using the same procedure as described in Step A of Preparation 1. The crude product was purified by flash column chromatography on silica gel eluting with Hexane: EtOAc (4:1) to give the title product (68% yield).

¹H NMR (CDCl₃, 300 MHz): δ 1.42 (m, 12H), 4.71 (bs, 1H), 4.83 (bs, 1H),6.0 (bs, 1H), 6.71 (d, J=8.0 Hz, 1H), 6.75 (s, 1H), 6.82 (d, J=7.8 Hz, 1H), 7.16 (t, J=7.8 Hz, 1H).

MS: (M+H)⁺238.

Step D: (S)-{1-[3-(Pyridin-2-yloxy)-phenyl]-ethyl}-carbamic acid tert-butyl ester A mixture of (S)-[1-(3-hydroxy-phenyl)-ethyl]-carbamic acid tert-butyl ester (10 g, 42.1 mmol), 2-bromopyridine (8 g, 50.6 mmol), potassium carbonate (powder, 14 g, 101 mmol) and copper iodide (325 mesh powder, 6 g, 31.6 mmol) was heated at 115° C. for 12 h. The reaction mixture was cooled to room temperature and concentrated in vacuo. CH₂Cl₂ (100 mL) was added, and the resulting reaction mixture was filtered. The filtrate was washed with H₂O (3×50 mL) followed by brine (100 ml), dried over anhydrous magnesium sulfate and concentrated in vacuo. The residue was purified by flash column chromatography on silica gel eluting with 2:1/Hexane:EtOAc to give the title product (12.1 g, 91% yield).

¹H NMR (CDCl₃,300 MHz): δ 1.41 (s, 9H), 1.45 (d, J=6.4 Hz, 3H), 4.79 (bs, 2H), 6.89 (d, J=8.2 Hz, 1H), 7.01 (m, 2H), 7.04 (s, 1H), 7.11 (d, 1H), 7.35 (t, J=7.8 Hz, 1H), 7.67 (m, 1H), 8.20 (m, 1H).

MS: (M+H)⁺315.

Step E: (S)-1-[3-(Pyridin-2-yloxyl)-phenyl]-ethylamine

A mixture of (S)-{1-[3-(pyridin-2-yloxy)-phenyl]-ethyl}-carbamic acid tert-butyl ester (5 g, 16 mmol), dioxane (80 mL) and HCl (64 mL, 4N) was stirred at 50° C. for 4 h and concentrated in vacuo then CH₂Cl₂ (100 mL) was added and the reaction mixture was basified with NaOH (5N) followed by extraction with CH₂Cl₂ (2×100 mL). The organic layer was washed with brine (100 mL), dried over anhydrous magnesium sulfate and filtered, and the filtrate was concentrated to give the title compound (3.39 g, 99% yield).

¹H NMR (CDCl₃, 300 MHz): δ 1.39 (d, J=6.6 Hz, 3H), 1.70 (s, 2H), 4.12 (q, J=6.6 Hz, 1H), 6.87 (d, J=8.3 Hz, 1H), 7.0 (m, 2H), 7.13 (s, 1H), 7.17 (d, J=7.7 Hz, 1H), 7.36 (t, J=7.8 Hz, 1H), 7.68 (m, 1H), 8.19 (m, 1H).

MS: (M+H)⁺215.

Preparation 2

Preparation of (S)-1-[3-(pyridin-3-yloxy)-phenyl-ethylamine

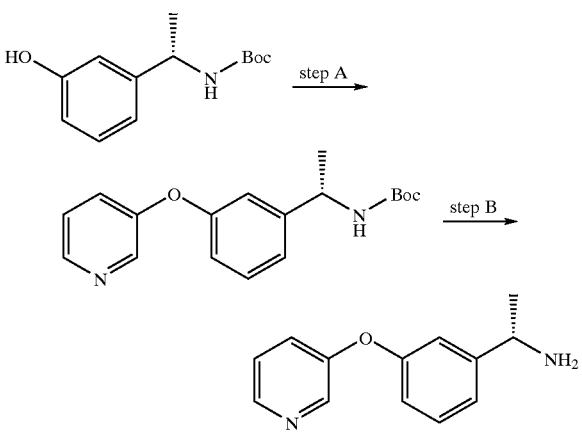

Step A: (S)-{1-[3-(Pyridin-3-yloxy)-phenyl]-ethyl}-carbamic acid tert-butyl ester A mixture of (S)-[1-(3-hydroxy-phenyl)-ethyl]-carbamic acid tert-butyl ester (10 g, 42.1 mmol), 3-bromopyridine (8 g, 50.6 mmol), potassium carbonate (powder, 14 g, 101 mmol) and copper iodide (325 mesh powder, 6 g, 31.6 mmol) was heated at 115° C. for 48 h. The reaction mixture was cooled to room temperature and concentrated in vacuo then CH₂Cl₂ (100 mL) was added, the reaction mixture was filtered, and the filtrate was washed with H₂O (3×50 mL) and brine (100 mL), dried over anhydrous magnesium sulfate and concentrated in vacuo. The residue was purified by flash column chromatography on silica gel eluting with 2:1/Hexane:EtOAc to give the title product (6.4 g, 48% yield).

¹H NMR (CDCl₃, 300 MHz): δ 1.40 (s, 9H), 1.42 (d, J=9.0 Hz, 3H), 4.78 (bs, 2H), 6.88 (m, 1H), 6.97 (t, J=2.0 Hz, 1H), 7.09 (d, J=7.7 Hz, 1H), 7.29 (m, 3H), 8.38 (bs, 2H).

MS: (M+H)⁺315.

Step B: (S)-1-[3-(Pyridin-3-yloxy)-phenyl-ethylamine

A mixture of (S)-{1-[3-(pyridin-3-yloxy)-phenyl]-ethyl}-carbamic acid tert-butyl ester (3.0 g, 9.5 mmol), dioxane (50 mL) and HCl (40 mL, 4N) was stirred at 50° C. for 4 h and then concentrated in vacuo then CH₂Cl₂ (100 ml) was added. The reaction mixture was basified with NaOH (5N) followed by extraction with CH₂Cl₂ (100 mL), and the organic layer was washed with brine (50 mL), dried over anhydrous magnesium sulfate and filtered. The filtrate was concentrated to give the title compound (1.82 g, 89% yield).

¹H NMR (CDCl₃, 300 MHz): δ 1.26 (d, J=6.6 Hz, 3H), 1.53 (bs, 2H), 4.01 (q, J=6.6 Hz, 1H), 6.78 (m, 1H), 6.97 (m, 1H), 7.04 (d, J=7.7 Hz, 1H), 7.17 (m, 3H), 8.24 (m, 1H), 8.30 (d, J=2.4 Hz, 1H).

MS: (M+H)⁺215.

Preparation 3

Preparation of (S)-1-[3-(6-methyl-pyridin-3-yloxy)-phenyl]-ethylamine

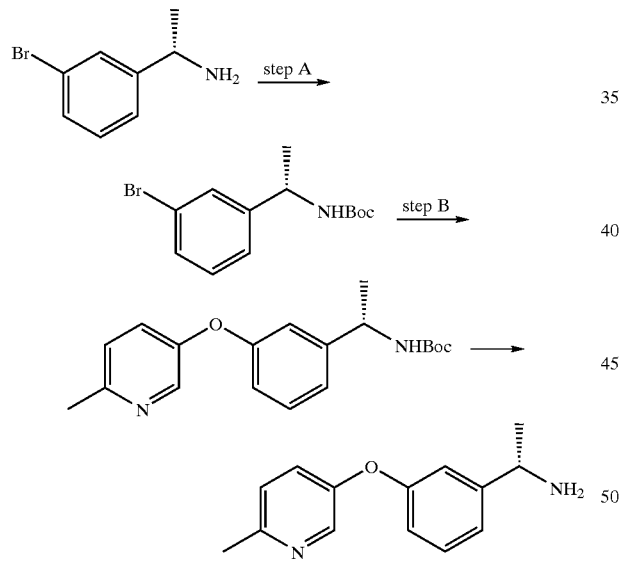

Step A: (S)-[1-(3-Bromo-phenyl)-ethyl]-carbamic acid tert-butyl ester (S)-3-Bromo-ethylphenylamine (20 g, 0.1 mol), di-tert-butyl dicarbonate (21.8 g, 0.1 mol) and Et₃N (27.8 mL, 0.2 mol) in CH₂Cl₂ (100 mL) was stirred at room temperature for 12 h. The reaction solution was washed with saturated NaHCO₃, the organic layer was separated, and the aqueous layer was extracted with CH₂Cl₂ three times. The combined organic layers were dried over anhydrous magnesium sulfate, filtered and the filtrate was concentrated in vacuo to provide the title compound (26 g, 87% yield) as white solid.

¹H NMR (CDCl₃, 400 MHz): δ 1.42 (m, 12H), 4.75 (bs, 2H), 7.21 (m, 2H), 7.37 (m, 1H), 7.43 (m, 1H).

Step B: (S)-{1-[3-(6-Methyl-pyridin-3-yloxy)-phenyl]-ethyl}-carbamic acid tert-butyl Ester A mixture of (S)-[1-(3-bromo-phenyl)-ethyl]-carbamic acid tert-butyl ester (10 g, 33.3 mol), 5-hydroxy-2-methylpyridine (4 g, 36.7 mol), copper iodide (6.3 g, 33.3 mol), potassium carbonate (9.2 g, 66.7 mol) and pyridine (33 mL) in sealed tube was heated at 145° C. for six days. The reaction was cooled down to room temperature and filtered, the filtrate was washed with H₂O and extracted with CH₂Cl₂ three times, and the combined organic layers were dried over anhydrous magnesium sulfate and concentrated in vacuo. The residue was purified by flash column chromatography on silica gel eluting with 30:20:1/Hexane:EtOAc:triethylamine to give the title product (3.8 g, 33% yield) as sticky yellow oil.

¹H NMR (MeOD, 400 MHz): δ 1.36 (d, J=7.1 Hz, 3H), 1.39 (s, 9H), 2.50 (s, 3H), 4.28 (bd, 2H), 6.87 (dd, J=8.0 Hz, J=1.8 Hz, 1H), 6.97 (m, 1H), 7.11 (d, J=7.7 Hz, 1H), 7.26–7.36 (m, 3H), 8.15 (d, J=1.4 Hz, 1H).

Step C: (S)-1-[3-(6-Methyl-pyridin-3-yloxy)-phenyl]-ethylamine (S)-{1-[3-(6-Methyl-pyridin-3-yloxy)-phenyl]-ethyl}-carbamic acid tert-butyl ester (3.45 g, 10.52 mmol), hydrogen chloride in ether (36.8 mL, 1.0M) and methanol (5 mL) was stirred at room temperature for 6 h. The reaction mixture was concentrated in vacuo to provide the title compound (3.4 g, quantitative yield) as yellow solid.

¹H NMR (MeOD, 400 MHz): δ 1.66 (d, 3H), 2.78 (s, 3H), 4.53 (bs, 1H), 7.25–7.59 (m, 4H), 7.91 (s, 1H), 8.14 (s, 1H), 8.54 (s, 1H).

Preparation 4

Preparation of (S)-1-[3-(pyridin-4-yloxy)-phenyl-ethylamine

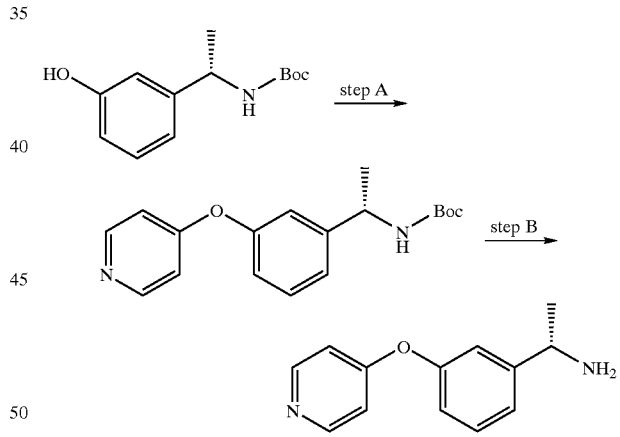

Step A: (I)-1-[3-(Pyridin-4-yloxy)-phenyl]-ethyl]-carbamic acid tert-butyl ester A mixture of (S)-[1-(3-hydroxy-phenyl)-ethyl]-carbamic acid tert-butyl ester (10 g, 42.1 mmol), 4-bromopyridine (8 g, 50.6 mmol), potassium carbonate (powder, 14 g, 101 mmol) and copper iodide (325 mesh powder, 6 g, 31.6 mmol) was heated at 115° C. for 24 h. The reaction mixture was cooled to room temperature and concentrated in vacuo then CH₂Cl₂ (100 mL) was added. The reaction mixture was filtered, and the filtrate was washed with H₂O (3×50 mL) and brine (100 mL), dried over anhydrous magnesium sulfate and concentrated in vacuo. The residue was purified by flash column chromatography on silica gel eluting with 2:1/Hexane:EtOAc to give the title product (10.4 g, 78% yield).

¹H NMR (CDCl₃, 300 MHz): δ 1.40 (s, 9H), 1.43 (d, J=6.8 Hz, 3H), 4.78 (bs, 1H), 4.84 (bs, 1H), 6.96 (d, J=7.9 Hz, 1H), 7.03 (s, 1H), 7.18 (d, J=7.6 Hz, 1H), 7.37 (t, J=7.8 Hz, 1H).

MS: (M+H)⁺315.

Step B: (S)-1-[3-(Pyridin-4-yloxy)-phenyl-ethylamine

A mixture of (S)-{1-[3-(pyridin-4-yloxy)-phenyl]-ethyl}-carbamic acid tert-butyl ester (3.0 g, 9.5 mmol), dioxane (50 mL) and HCl (40 mL, 4N) was stirred at 50° C. for 5 h and concentrated in vacuo. CH₂Cl₂ (100 mL) was added and the reaction mixture was basified with NaOH(SN) followed by extraction with CH₂Cl₂ (100 mL). The organic layer was washed with brine (50 mL), dried over anhydrous magnesium sulfate and filtered, and the filtrate was concentrated to give the title compound (1.26 g, 62% yield).

¹H NMR (CDCl₃,300 MHz): δ 1.38 (d, J=5.4 Hz, 3H), 4.20 (bs, 1H), 6.84 (s, 2H), 6.94 (m, 2H), 7.09 (s, 1H), 7.21 (d, J=7.7 Hz, 1H), 7.36 (t, J=7.8 Hz, 2H), 8.49 (bs, 2H).

Preparation 5
Preparation of (S)-1-[3-(pyrazin-2-yloxy)-phenyl]-ethylamine

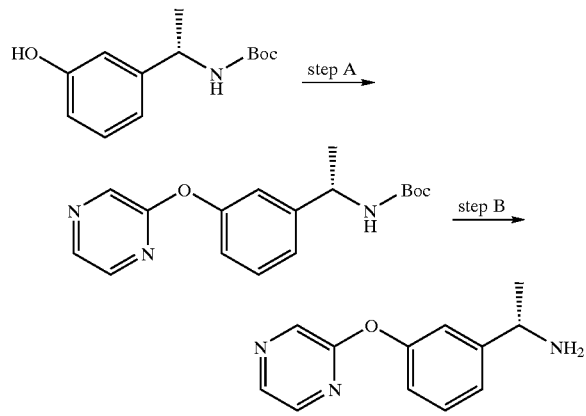

Step A: (S)-{1-[3-(pyrazin-2-yloxy)-phenyl]-ethyl}-carbamic Acid tert-butyl Ester A mixture of (S)-[1-(3-hydroxy-phenyl)-ethyl]-carbamic acid tert-butyl ester (1 g, 4.2 mmol), 2-chloro-pyrazine (0.58 g, 5.1 mmol), potassium carbonate (powder, 1.4 g, 10.1 mmol), copper iodide (325 mesh powder, 0.6 g, 3.2 mmol) and pyridine (5 mL) was heated at 115° C. for 24 h. CH₂Cl₂ (100 mL) was added, and the reaction mixture was diluted with CH₂Cl₂ (100 mL), filtered through celite, and rinse with CH₂Cl₂ (2×50 mL). The filtrate was concentrated in vacuo and the residue was purified by flash column chromatography on silica gel eluting with 1:1/Hexane:EtOAc to give the title product (1.5 g, quantitative yield).

MS: (M+H)⁺316.

Step B: (S)-1-[3-(Pyrazin-2-yloxy)-phenyl]-ethylamine

A mixture of (S)-{1-[3-(pyrazin-2-yloxy)-phenyl]-ethyl}-carbamic acid tert-butyl ester (1.33 g, 4.2 mmol), dioxane (20 mL) and HCl (4.2 mL, 4N) was stirred at 50° C. for 5 h and concentrated in vacuo. CH₂Cl₂ (50 mL) was added and the reaction mixture was basified with NaOH (5N) followed by extraction with CH₂Cl₂ (2×50 mL). The organic layer was washed with brine (50 mL), dried over anhydrous magnesium sulfate and filtered, and the filtrate was concentrated to give the title compound (0.77 g, 85% yield).

¹H NMR (CDCl₃, 300 MHz): δ 1.41 (d, J=6.2 Hz, 3H), 2.63 (bs, 2H), 4.20 (bs, 1H), 7.01 (m, 1H), 7.17 (s, 1H), 7.24 (d, J=7.9 Hz, 1H), 7.37 (t, J=7.9 Hz, 1H), 8.08 (m, 1H), 8.24 (m, 1H), 8.40 (m, 1H).

MS: (M+H)⁺216.

Preparation 6
Preparation of (S)-1-[3-(pyrimidin-2-yloxy)-phenyl]-ethylamine

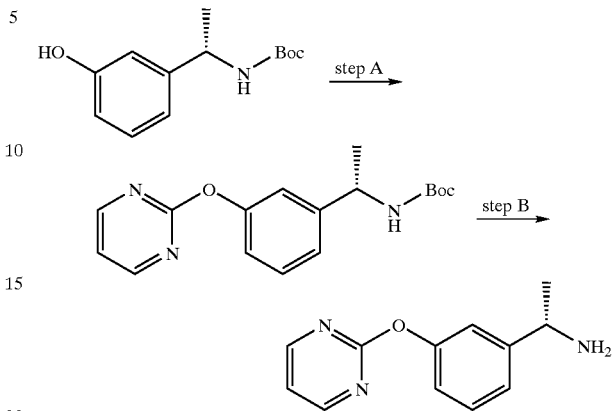

Step A: (S)-{1-[3-(Pyrimidin-2-yloxy)-phenyl]-ethyl}-carbamic acid tert-butyl ester A mixture of (S)-[1-(3-hydroxy-phenyl)-ethyl]-carbamic acid tert-butyl ester (1 g, 4.2 mmol), 2-bromo-pyrimidine (0.58 g, 5.1 mmol), potassium carbonate (powder, 1.4 g, 10.1 mmol), copper iodide (325 mesh powder, 0.6 g, 3.2 mmol) and pyridine (5 mL) was heated at 115° C. for 12 h. CH₂Cl₂ (100 mL) was added, the reaction mixture was filtered through celite and rinsed with CH₂Cl₂ (2×50 mL), and the filtrate was concentrated in vacuo. The residue was purified by flash column chromatography on silica gel eluting with 1:1/Hexane:EtOAc to give the title product (1.4 g, quantitative yield).

MS: (M+H)⁺316

Step B: (S)-1-[3-(Pyrimidin-2-yloxy)-phenyl]-ethylamine

A mixture of (S)-{1-[3-(pyrimidin-2-yloxy)-phenyl]-ethyl}-carbamic acid tert-butyl ester (1.33 g, 4.2 mmol), dioxane (20 mL) and HCl (4.2 mL, 4N) was stirred at 50° C. for 5 h and concentrated in vacuo. CH₂Cl₂ (50 mL) was added and the reaction mixture was basified with NaOH (5N) followed by extraction with CH₂Cl₂ (2×50 mL). The organic layer was washed with brine (50 mL), dried over anhydrous magnesium sulfate and filtered, and the filtrate was concentrated to give the title compound (0.72 g, 79% yield).

¹H NMR (CDCl₃, 300 MHz): δ 1.41 (d, J=6.6 Hz, 3H), 2.11 (bs, 2H), 4.17 (q, J=6.6 Hz, 1H), 7.05 (m, 2H), 7.22 (d, J=9.9 Hz, 1H), 7.39 (t, J=7.7 Hz, 1H), 8.56 (m, 3H).

MS: (M+H)⁺216.

Preparation 7
Preparation of (S)-1-[3-(pyrimidin-5-yloxy)-phenyl]-ethylamine

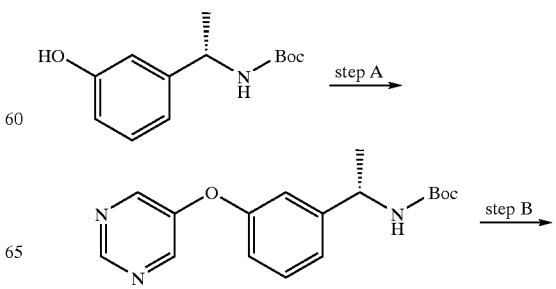

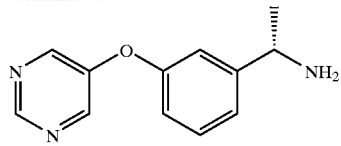

Step A: (S)-1-[3-(Pyrimidin-5-yloxy)-phenyl]-ethyl]-carbamic acid tert-butyl ester A mixture of (S)-[1-(3-hydroxy-phenyl)-ethyl]-carbamic acid tert-butyl ester (1 g, 4.2 mmol), 5-bromo-pyrimidine (0.8 g, 5.1 mmol), potassium carbonate (powder, 1.4 g, 10.1 mmol), copper iodide (325 mesh powder, 0.6 g, 3.2 mmol) and pyridine (5 mL) was heated at 115° C. for 24 h. $CH_2Cl_2$ (100 mL) was added, the reaction mixture was filtered through celite, rinsed with $CH_2Cl_2$ (2×50 mL), and the filtrate was concentrated in vacuo. The residue was purified by flash column chromatography on silica gel eluting with 1:1/Hexane:EtOAc to give the title product (0.81 g, 61% yield).

MS: $(M+H)^+$316.

Step B: (S)-1-[3-(pyrimidin-5-yloxy)-phenyl]-ethylamine

A mixture of (S)-{1-[3-(pyrimidin-5-yloxy)-phenyl]-ethyl}-carbamic acid tert-butyl ester (0.81 g, 2.6 mmol), dioxane (20 mL) and HCl (2.6 mL, 4N) was stirred at 50° C. for 5 h and concentrated in vacuo. $CH_2Cl_2$ (50 mL) was added and the reaction mixture was basified with NaOH (5N) followed by extraction with $CH_2Cl_2$ (2×50 mL). The organic layer was washed with brine (50 mL), dried over anhydrous magnesium sulfate and filtered, and the filtrate was concentrated to give the title compound (0.52 g, 95% yield).

MS: $(M+H)^+$216

Preparation 8

Preparation of (S)-[3-(1-amino-ethyl)-phenyl]-pyridin-3-ylmethyl-amine

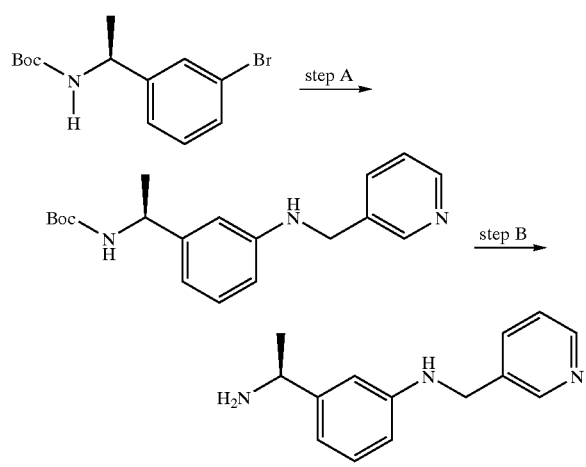

Step A: (S)-(1-{3-[(Pyridin-3-ylmethyl)-amino]phenyl}-ethyl)-carbamic acid tert-butyl ester A mixture of (S)-[1-(3-bromo-phenyl)-ethyl]-carbamic acid tert-butyl ester (3 g), (3-aminomethyl)pyridine (10 g), $Pd_2(dba)_3$ (915 mg), di-t-butylbiphenylphosphine (298 mg), $K_3PO_4$ (4.24 g) in DME (60 mL) was stirred at reflux for 4 h. The reaction mixture was cooled down to room temperature, diluted with methylene chloride, filtered and concentrated to give a crude product. The crude product was purified by flash chromatography using Biotage eluting with ethyl acetate to give the desired product (3.1 g) as a solid.

$^1$H NMR (CDCl$_3$): 8.62 (d, J=1.7 Hz, 1H), 8.54 (dd, J=4.8, 1.7 Hz, 1H), 7.70–7.67 (m, 1H), 7.28–7.24 (m, 1H), 7.16 (t, J=7.8 Hz, 1H), 6.69 (d, J=7.59 Hz, 1H), 6.57 (s, 1H), 6.51 (dd, J=7.89, 1.68 Hz, 1H), 4.60 (br s, 2H), 4.35 (s, 2H), 4.05 (br s, 1H), 1.45 (s, 9H), 1.41 (d, J=6.3 Hz, 3H).

MS $(M+H)^+$328.

Step B: (S)-[3-(1-Amino-ethyl)-phenyl]-pyridin-3-ylmethyl-amine

A mixture of (S)-(1-{3-[(pyridin-3-ylmethyl)-amino]-phenyl}-ethyl)carbamic acid tert-butyl ester (3 g) and 9 mL of 4 N HCl in dioxane (20 mL) was heated at 60° for 2 h. The reaction mixture was concentrated in vacuo, and the residue was neutralized with 10 N NaOH followed by extraction with methylene chloride. The organic layer was washed with brine, dried over $Na_2SO_4$, and concentrated in vacuo to give the title compound (1.9 g) as an oil.

$^1$H NMR (CDCl$_3$): 8.63 (d, J=2.04 Hz, 1H), 8.53 (dd, J=4.77, 1.35 Hz, 1H), 7.71 (dd, J=7.68, 1.38 Hz, 1H), 7.28–7.10 (m, 1H), 7.16 (t, J=7.8 Hz, 1H), 6.72 (d, J=7.6 Hz, 1H), 6.65 (d, J=1.89 Hz, 1H), 6.51 (dd, J=8.01, 2.37 Hz, 1H), 4.37 (d, J=5.58 Hz, 2H), 4.09 (s, 2H), 4.06 (q, J=6.6 Hz, 1H), 1.41 (d, J=6.6 Hz, 3H).

MS $(M+H)^+$228.

Preparation 9

Preparation of (S)-[3-(1-amino-ethyl)-phenyl]-pyridin-4-yl-amine

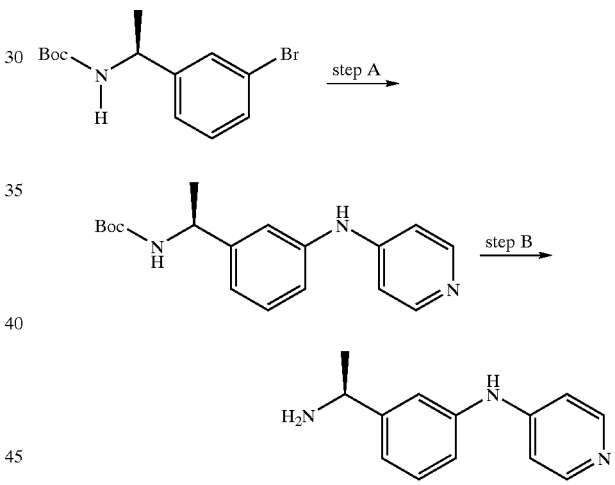

Step A: (S)-1-[3-(Pyridin-4-ylamino)-phenyl]-ethyl]-carbamic acid tert-butyl ester A mixture of (S)-[1-(3-bromo-phenyl)-ethyl]-carbamic acid tert-butyl ester (3 g), 4-aminopyridine (1.88 g), $Pd_2(dba)_3$ (915 mg), di-t-butylbiphenylphosphine (298 mg), $K_3PO_4$ (4.24 g) in DME (20 mL) was stirred under reflux for 24 h. The reaction mixture was cooled down to room temperature, diluted with methylene chloride, filtered and concentrated in vacuo. The resulting residue was purified by flash chromatography using Biotage eluting with 5% MeOH in ethyl acetate to give the desired product (2.2 g) as a solid.

$^1$H NMR (CDCl$_3$): 8.28 (dd, J=4.8, 1.5 Hz, 2H), 7.34 (t, J=7.8 Hz, 1H), 7.10–7.04 (m, 3H), 6.81 (dd, J=4.8, 1.5 Hz, 2H), 6.15 (s, 1H), 4.77 (br s, 2H), 1.45 (s, 9H), 1.41 (d, J=6.4 Hz, 3H).

MS $(M+H)^+$314.

Step B: (S)-[3-(1-Amino-ethyl)-phenyl]-pyridin-4-yl-amine

A mixture of (S)-1-[3-(pyridin-4-ylamino)-phenyl]-ethyl}-carbamic acid tert-butyl ester (2.17 g) and 7 ml of 4 N HCl in dioxane (20 mL) was heated at 60° C. for 2 h. The reaction mixture was concentrated in vacuo, and the residue was neutralized with 10 N NaOH followed by extraction with methylene chloride. The organic layer was washed with brine, dried over $Na_2SO_4$, and concentrated to give the title compound (1.39 g) as an oil.

$^1$H NMR (CDCl$_3$): 8.29 (d, J=6.0 Hz, 2H), 7.34–7.06 (m, 4H), 6.79 (d, J=6.0 Hz, 2H), 6.19 (s, 1H), 4.15 (t, J=6.5 Hz, 1H), 1.41 (d, J=6.5 Hz, 3H).

EXAMPLES

Example 1

3-phenyl-N-{1-[3-(pyridin-2-yloxyl)-phenyl]-ethyl}-acrylamide

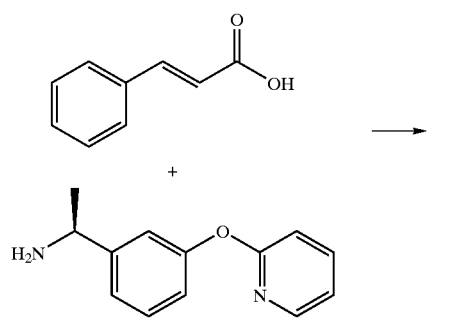

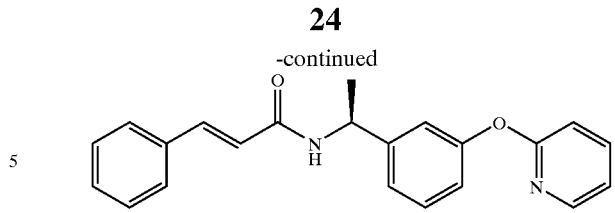

A mixture of cinnamic acid (0.11 mmol), 1-[3-(pyridine-2-yloxyl)phenyl]-ethylamine (16.3 mg, 0.11 mmol), EDAC.HCl (42 mg, 0.22 mmol), DMAP (13 mg, 0.11 mmol) and Et$_3$N (0.1 mL, 0.44 mmol) in CH$_2$Cl$_2$ (2 mL) was stirred at room temperature for 12 h. The reaction mixture was purified by flash column chromatography on silica gel eluting with 1:1/Hexane:EtOAc to give the title compound.

$^1$H NMR (CDCl$_3$, 300 MHz): δ 1.56 (d, J=6.9 Hz, 3H), 5.30 (m, 1H), 5.98 (d, J=7.7 Hz, 1H), 6.38 (d, J=15.6 Hz, 1H), 6.91 (d, J=8.3 Hz, 1H), 7.04 (m, 2H), 7.14 (s, 1H), 7.24 (d, J=12.8 Hz, 1H), 7.35 (m, 4H), 7.47 (m, 2H), 7.63 (d, J=15.8 Hz, 1H), 7.66 (m, 1H), 8.18 (m, 1H).

$^{13}$NMR (CDCl$_3$, 75 MHz): δ 21.4, 48.6, 111.8, 118.6, 119.0, 120.1, 120.7, 127.8, 128.8, 129.7, 129.9, 134.9, 139.5, 141.3, 145.0, 147.7, 154.6, 163.6, 165.0.

MS(M+H)$^+$345.

Examples 2–13

Examples 2–13 were made from the appropriate acids using the general procedures as described for Example 1.

| Example No. | Structure | Chemical Name | HPLC rt (min), method | Mass (M + H)$^+$ m/z |
|---|---|---|---|---|
| 2 | 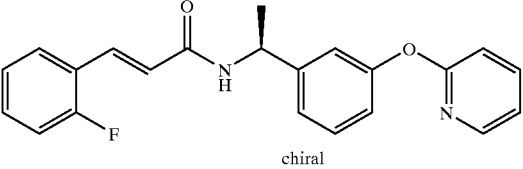 chiral | (S)-3-(2-Fluoro-phenyl)-N-{1-[3-(pyridin-2-yloxy)-phenyl]-ethyl}-acrylamide | 2.280 (b) | 363 |
| 3 | 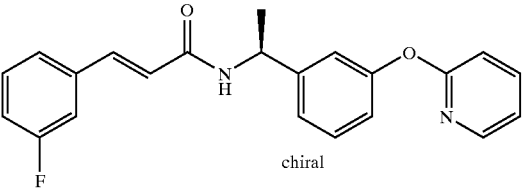 chiral | (S)-3-(3-Fluoro-phenyl)-N-{1-[3-(pyridin-2-yloxy)-phenyl]-ethyl}-acrylamide | 2.327 (b) | 363 |
| 4 | 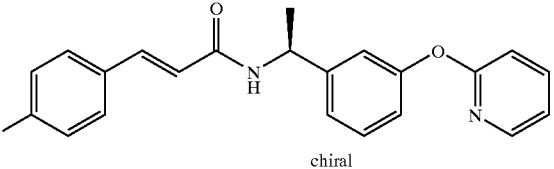 chiral | (S)-3-(4-Fluoro-phenyl)-N-{1-[3-(pyridin-2-yloxy)-phenyl]-ethyl}-acrylamide | 2.293 (b) | 363 |
| 5 | 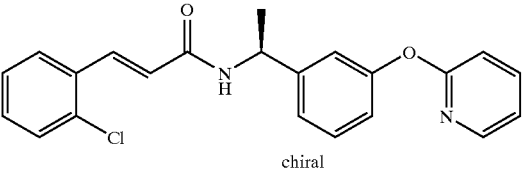 chiral | (S)-3-(2-Chloro-phenyl)-N-{1-[3-(pyridin-2-yloxy)-phenyl]-ethyl}-acrylamide | 2.403 (b) | 379 |

-continued

| Example No. | Structure | Chemical Name | HPLC rt (min), method | Mass (M + H)+ m/z |
|---|---|---|---|---|
| 6 | 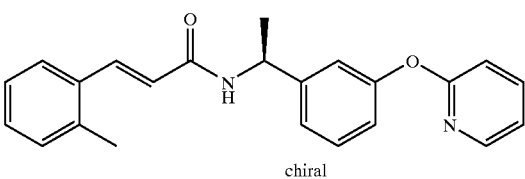 | (S)-N-{1-[3-(Pyridin-2-yloxy)-phenyl]-ethyl}-3-o-tolyl-acrylamide | 1.580 (a) | 359 |
| 7 | 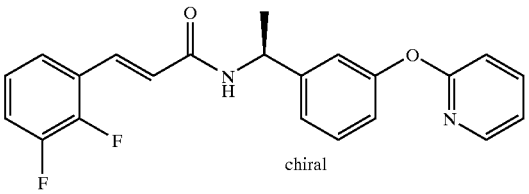 | (S)-3-(2,3-Difluorophenyl)-N-{1-[3-(pyridin-2-yloxy)-phenyl]-ethyl}-acrylamide | 1.590 (a) | 381 |
| 8 | 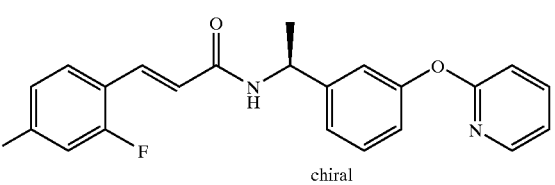 | (S)-3-(2,4-Difluorophenyl)-N-{1-[3-(pyridin-2-yloxy)-phenyl]-ethyl}-acrylamide | 1.573 (a) | 381 |
| 9 | 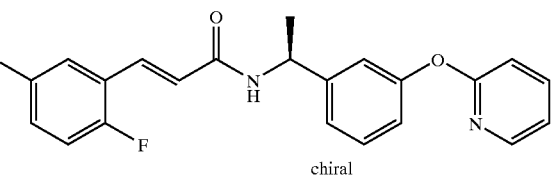 | (S)-3-(2,5-Difluorophenyl)-N-{1-[3-(pyridin-2-yloxy)-phenyl]-ethyl}-acrylamide | 1.557 (a) | 381 |
| 10 | 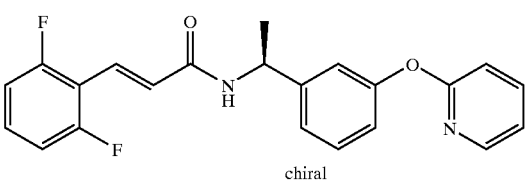 | (S)-3-(2,6-Difluorophenyl)-N-{1-[3-(pyridin-2-yloxy)-phenyl]-ethyl}-acrylamide | 1.547 (a) | 381 |
| 11 | 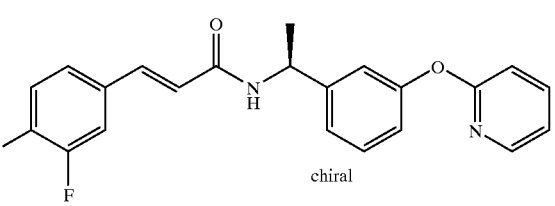 | (S)-3-(3,4-Difluorophenyl)-N-{1-[3-(pyridin-2-yloxy)-phenyl]-ethyl}-acrylamide | 1.573 (a) | 381 |
| 12 | 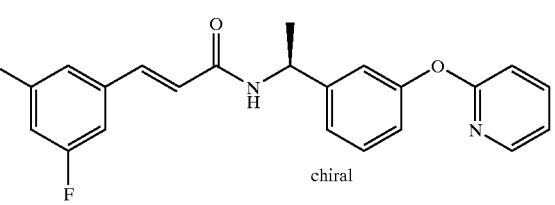 | (S)-3-(3,5-Difluorophenyl)-N-{1-[3-(pyridin-2-yloxy)-phenyl]-ethyl}-acrylamide | 1.597 (a) | 381 |

| Example No. | Structure | Chemical Name | HPLC rt (min), method | Mass (M + H)+ m/z |
|---|---|---|---|---|
| 13 | 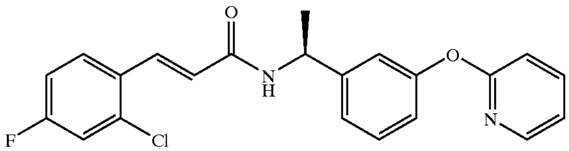 | (S)-3-(2-Chloro-4-fluoro-phenyl)-N-{1-[3-(pyridin-2-yl-oxy)-phenyl]-ethyl}-acrylamide | 2.467 (b) | 397 |

Example 14
(S)-phenyl-N-{1-[3-(pyridin-3-yloxyl)-phenyl]ethyl}-acrylamide

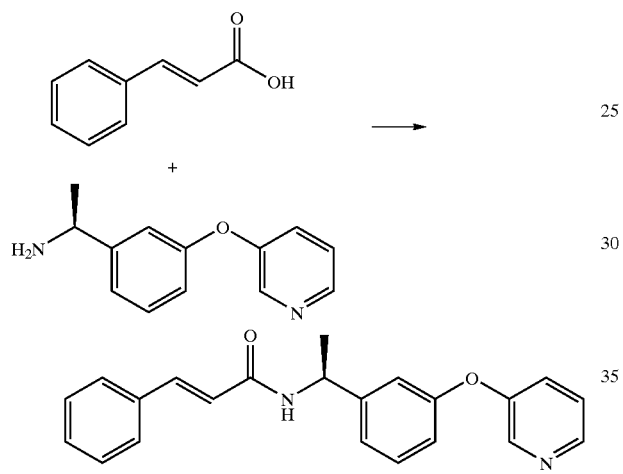

The title compound was prepared following the general procedures as described for Example 1 with the exception that (S)-1-[3-(pyridine-3-yloxyl)-phenyl]-ethylamine was used.

$^1$H NMR (CDCl$_3$, 300 MHz): δ 1.53 (d, J=6.9 Hz, 3H), 5.25 (m, 1H), 6.06 (d, J=7.6 Hz, 1H), 6.67 (d, J=15.6 Hz, 1H), 6.90 (d, 1H), 7.05 (d, 1H), 7.17 (d, 1H), 7.47 (m, 2H), 7.63 (d, J=15.6 Hz, 1H), 8.38 (d, J=11.4 Hz, 2H).

$^{13}$C NMR(CDCl$_3$,75 MHz): δ 21.9, 48.7, 116.8, 117.5, 120.5, 122.0, 124.1, 125.5, 127.8, 128.8, 129.7, 130.3, 134.8, 141.5, 144.5, 145.9, 153.8, 156.7, 165.0.

MS (M+H)$^+$345.

Examples 15–24

Examples 15–24 were made from the appropriate acids using the general procedures as described for Example 14.

| Example No. | Structure | Chemical Name | HPLC rt (min), method | Mass (M + H)+ m/z |
|---|---|---|---|---|
| 15 | 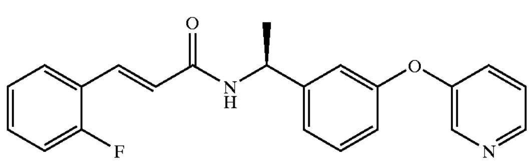 | (S)-3-(2-Fluoro-phenyl)-N-{1-[3-(pyridin-3-yloxy)-phenyl]-ethyl}-acrylamide | 1.247 (a) | 363 |
| 16 | 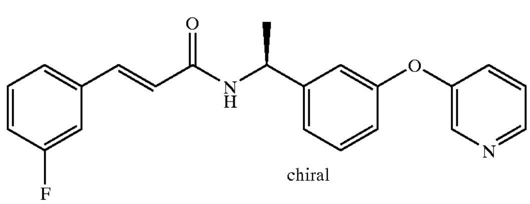 | (S)-3-(3-Fluoro-phenyl)-N-{1-[3-(pyridin-3-yloxy)-phenyl]-ethyl}-acrylamide | 1.236 (a) | 363 |

-continued

| Example No. | Structure | Chemical Name | HPLC rt (min), method | Mass (M + H)+ m/z |
|---|---|---|---|---|
| 17 | 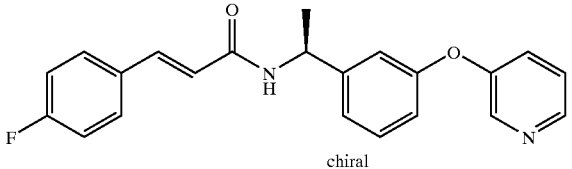 | (S)-3-(4-Fluoro-phenyl)-N-{1-[3-(pyridin-3-yloxy)-phenyl]-ethyl}-acrylamide | 1.253 (a) | 363 |
| 18 | 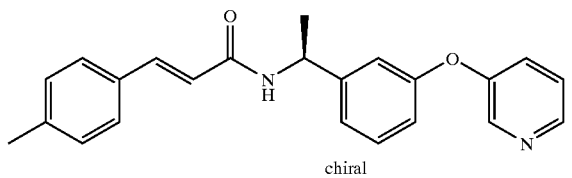 | (S)-N-{1-[3-(Pyridin-3-yloxy)-phenyl]-ethyl}-3-p-tolyl-acrylamide | 1.337 (a) | 359 |
| 19 | 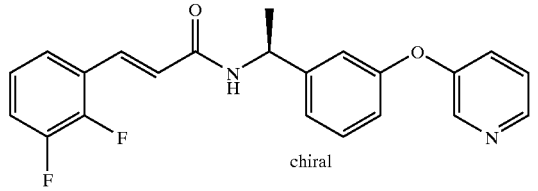 | (S)-3-(2,3-Difluoro-phenyl)-N-{1-[3-(pyridin-3-yloxy)-phenyl]-ethyl}-acrylamide | 1.320 (a) | 381 |
| 20 | 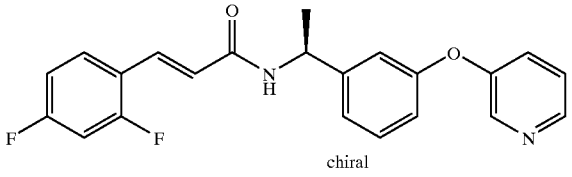 | (S)-3-(2,4-Difluoro-phenyl)-N-{1-[3-(pyridin-3-yloxy)-phenyl]-ethyl}-acrylamide | 1.310 (a) | 381 |
| 21 | 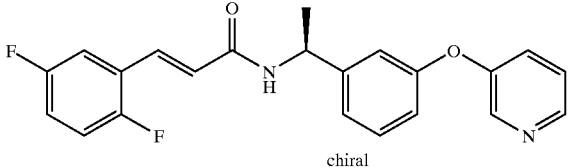 | (S)-3-(2,5-Difluoro-phenyl)-N-{1-[3-(pyridin-3-yloxy)-phenyl]-ethyl}-acrylamide | 1.280 (a) | 381 |
| 22 | 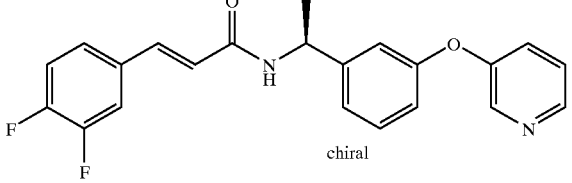 | (S)-3-(3,4-Difluoro-phenyl)-N-{1-[3-(pyridin-3-yloxy)-phenyl]-ethyl}-acrylamide | 1.350 (a) | 381 |
| 23 | 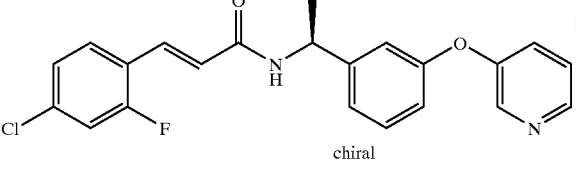 | (S)-3-(4-Chloro-2-fluoro-phenyl)-N-{1-[3-(pyridin-3-yloxy)-phenyl]-ethyl}-acrylamide | 1.440 (a) | 397 |

-continued

| Example No. | Structure | Chemical Name | HPLC rt (min), method | Mass (M + H)+ m/z |
|---|---|---|---|---|
| 24 | 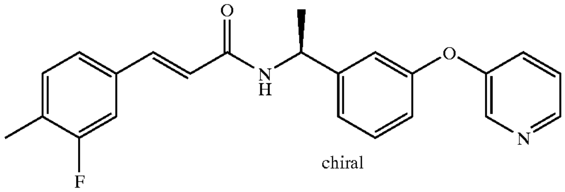 | (S)-3-(3-Fluoro-4-methyl-phenyl)-N-{1-[3-(pyridin-3-yl-oxy)-phenyl]-ethyl}-acrylamide | 1.407 (a) | 377 |
| 25 | 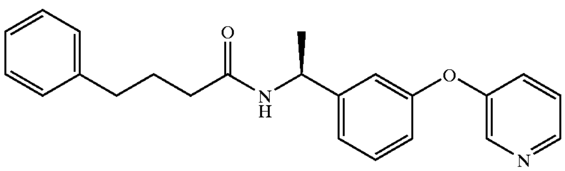 | (S)-4-Phenyl-N-[1-(3-pyridin-3-yl-phenyl)-ethyl]-butyramide | 1.40 (c) | 344 |

Example 26

(S)-3-(2-fluoro-phenyl)-N-{1-[3-(6-methyl-pyridin-3-yloxy)-phenyl]ethyl}-acrylamide

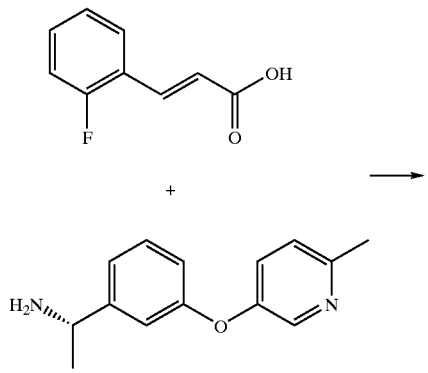

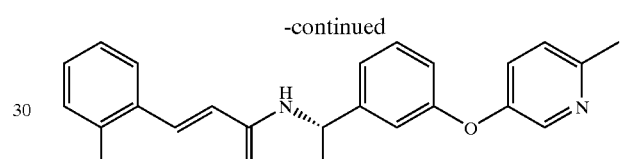

The title compound was prepared from 2-fluorocinnamic acid following the general procedures as described for Example 1 with the exception that (S)-1-[3-(6-methyl-pyridin-3-yloxy)-phenyl]ethylamine was used.

$^1$H NMR (CDCl$_3$, 400 MHz): δ 1.53 (d, J=6.8 Hz, 3H), 2.58 (s, 3H), 5.26 (q, J=7.2 Hz, 1H), 6.13 (d, J=7.6 Hz, 1H), 6.54 (d, J=16, 1H), 6.89–7.46 (m, 10H), 7.69 (d, J=16 Hz, 1H), 8.36 (d, J=2.8 Hz, 1H).

MS: (M+H)$^+$377.

Examples 27–34

Examples 27–34 were prepared from the appropriate acids following the general procedures as described for Example 26.

| Example No. | Structure | Chemical Name | HPLC rt (min), method | Mass (M + H)+ m/z |
|---|---|---|---|---|
| 27 | 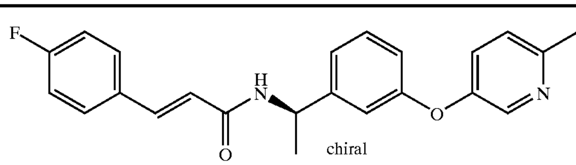 | (S)-3-(4-Fluoro-phenyl)-N-{1-[3-(6-methyl-pyridin-3-yloxy)-phenyl]-ethyl}-acrylamide | 1.25 (c) | 377 |
| 28 | 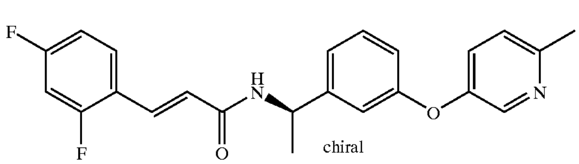 | (S)-3-(2,4-Difluoro-phenyl)-N-{1-[3-(6-methyl-pyridin-3-yloxy)-phenyl]-ethyl}-acrylamide | 1.30 (c) | 395 |

-continued

| Example No. | Structure | Chemical Name | HPLC rt (min), method | Mass (M + H)+ m/z |
|---|---|---|---|---|
| 29 | 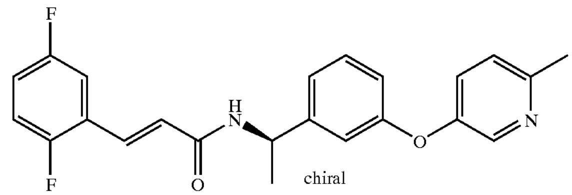 | (S)-3-(2,5-Difluoro-phenyl)-N-{1-[3-(6-methyl-pyridin-3-yloxy)-phenyl]-ethyl}-acrylamide | 1.29 (c) | 395 |
| 30 | 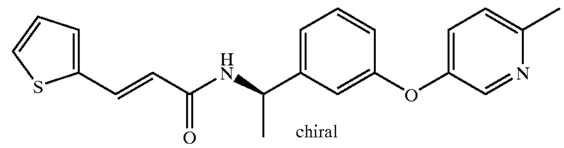 | (S)-N-{1-[3-(6-Methyl-pyridin-3-yloxy)-phenyl]-ethyl}-3-thiophen-2-yl-acrylamide | 1.18 (c) | 365 |
| 31 | 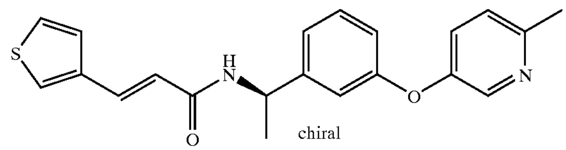 | (S)-N-{1-[3-(6-Methyl-pyridin-3-yloxy)-phenyl]-ethyl}-3-thiophen-3-yl-acrylamide | 1.15 (c) | 365 |
| 32 | 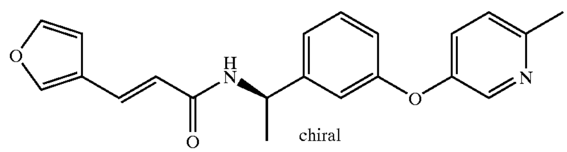 | (S)-3-Furan-3-yl-N-{1-[3-(6-methyl-pyridin-3-yl-oxy)-phenyl]-ethyl}-acrylamide | 1.07 (c) | 349 |
| 33 | 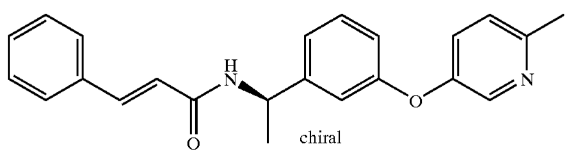 | (S)-N-{1-[3-(6-Methyl-pyridin-3-yloxy)-phenyl]-ethyl}-3-phenyl-acrylamide | 1.23 (c) | 359 |
| 34 | 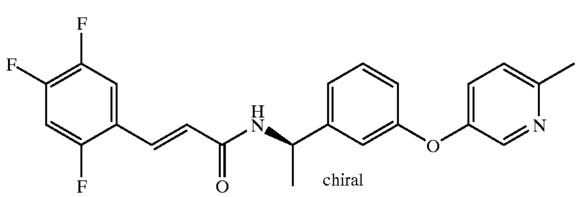 | (S)-N-{1-[3-(6-Methyl-pyridin-3-yloxy)-phenyl]-ethyl}-3-(2,4,5-trifluoro-phenyl)-acrylamide | 1.54 (c) | 413 |

Example 35

(S)-3-phenyl-N-{1-[3-(pyridin-4-yloxyl)-phenyl]-ethyl}-acrylamide

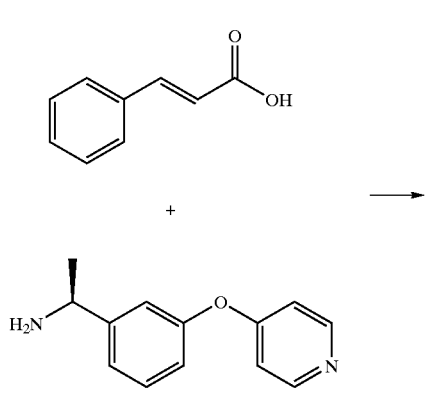

-continued

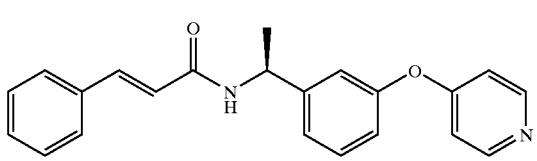

The title compound was prepared following the general procedures as described for Example 1 with the exception that (S)-1-[3-(pyridine-4-yloxyl)phenyl]-ethylamine was used.

$^1$H NMR (CDCl$_3$, 300 MHz): δ 1.54 (d, J=6.9 Hz, 3H), 5.28 (m, 1H), 6.23 (d, J=7.7 Hz, 1H), 6.42 (d, J=15.6 Hz, 1H), 6.82 (d, J=5.3 Hz, 2H), 6.97 (m, 1H), 7.09 (s, 1H), 7.26 (d, J=6.6 Hz, 1H), 7.34 (m, 4H), 7.46 (m, 2H), 7.63 (d, J=15.6 Hz, 1H), 8.44 (s, 2H).

$^{13}$C NMR (CDCl$_3$, 75 MHz): δ 21.9, 48.6, 112.3, 118.4, 119.5, 120.5, 123.3, 127.8, 128.8, 129.8, 130.4, 134.8, 141.5, 146.2, 151.4, 154.4, 164.6, 165.1.
MS (M+H)$^+$345.

Examples 36–53

Examples 36–53 were prepared from the appropriate acids following the general procedures as described for Example 35.

| Example No. | Structure | Chemical Name | HPLC rt (min), method | Mass (M + H)$^+$ m/z |
|---|---|---|---|---|
| 36 | 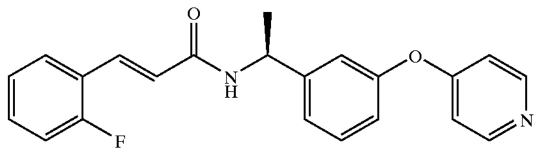 | (S)-3-(2-Fluoro-phenyl)-N-{1-[3-(pyridin-4-yloxy)-phenyl]-ethyl}-acrylamide | 1.203 (a) | 363 |
| 37 | 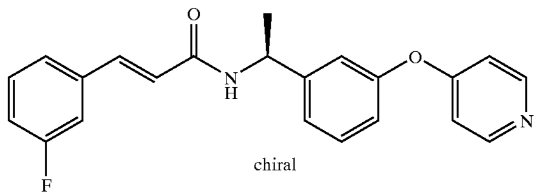 | (S)-3-(3-Fluoro-phenyl)-N-{1-[3-(pyridin-4-yloxy)-phenyl]-ethyl}-acrylamide | 1.217 (a) | 363 |
| 38 | 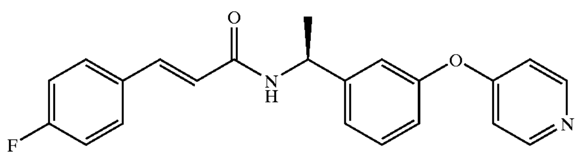 | (S)-3-(4-Fluoro-phenyl)-N-{1-[3-(pyridin-4-yloxy)-phenyl]-ethyl}-acrylamide | 1.203 (a) | 363 |
| 39 | 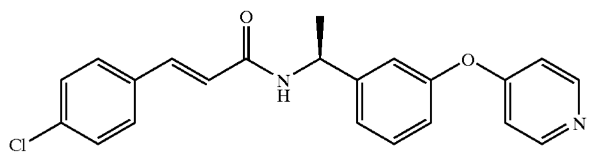 | (S)-3-(4-Chloro-phenyl)-N-{1-[3-(pyridin-4-yloxy)-phenyl]-ethyl}-acrylamide | 1.333 (a) | 379 |
| 40 | 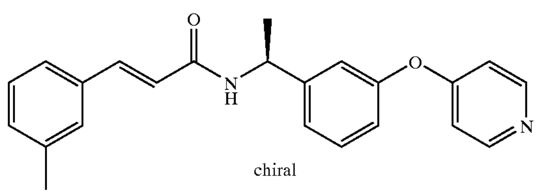 | (S)-N-{1-[3-(Pyridin-4-yloxy)-phenyl]-ethyl}-3-m-tolyl-acrylamide | 1.287 (a) | 359 |
| 41 | 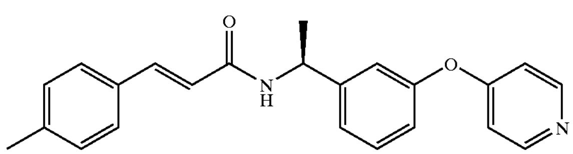 | (S)-N-{1-[3-(Pyridin-4-yloxy)-phenyl]-ethyl}-3-p-tolyl-acrylamide | 1.283 (a) | 359 |
| 42 | 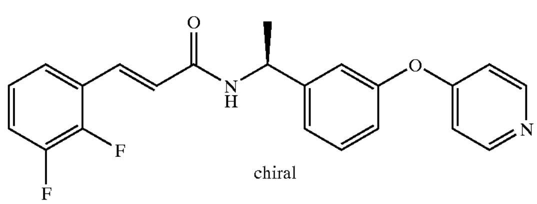 | (S)-3-(2,3-Difluoro-phenyl)-N-{1-[3-(pyridin-4-yloxy)-phenyl]-ethyl}-acrylamide | 1.250 (a) | 381 |

-continued

| Example No. | Structure | Chemical Name | HPLC rt (min), method | Mass (M + H)+ m/z |
|---|---|---|---|---|
| 43 | 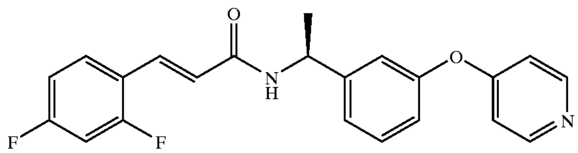 | (S)-3-(2,4-Difluoro-phenyl)-N-{1-[3-(pyridin-4-yl-oxy)-phenyl]-ethyl}-acryl-amide | 1.243 (a) | 381 |
| 44 | 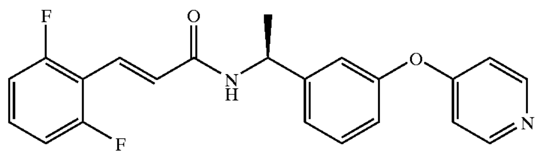 | (S)-3-(2,6-Difluoro-phenyl)-N-{1-[3-(pyridin-4-yl-oxy)-phenyl]-ethyl}-acryl-amide | 1.220 (a) | 381 |
| 45 | 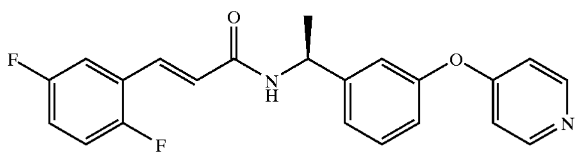 | (S)-3-(2,5-Difluoro-phenyl)-N-{1-[3-(pyridin-4-yl-oxy)-phenyl]-ethyl}-acryl-amide | 1.230 (a) | 381 |
| 46 | 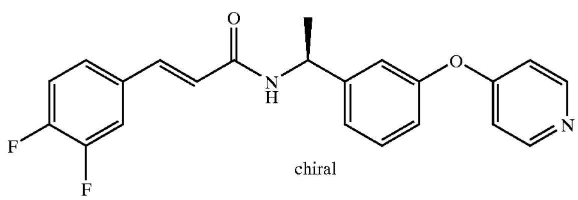 | (S)-3-(3,4-Difluoro-phenyl)-N-{1-[3-(pyridin-4-yl-oxy)-phenyl]-ethyl}-acryl-amide | 1.273 (a) | 381 |
| 47 | 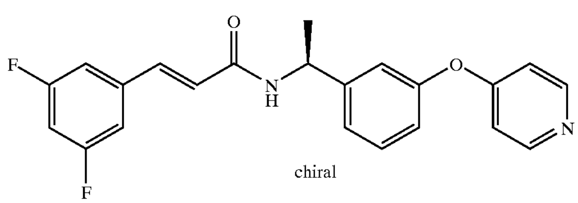 | (S)-3-(3,5-Difluoro-phenyl)-N-{1-[3-(pyridin-4-yl-oxy)-phenyl]-ethyl}-acryl-amide | 1.253 (a) | 381 |
| 48 | 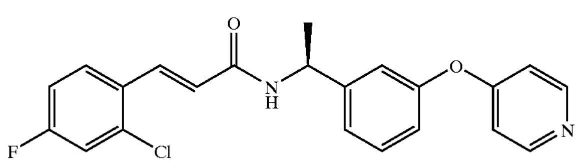 | (S)-3-(2-Chloro-4-fluoro-phenyl)-N-{1-[3-(pyridin-4-yl-oxy)-phenyl]-ethyl}-acryl-amide | 1.353 (a) | 397 |
| 49 | 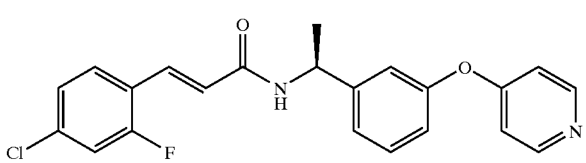 | (S)-3-(4-Chloro-2-fluoro-phenyl)-N-{1-[3-(pyridin-4-yl-oxy)-phenyl]-ethyl}-acryl-amide | 1.390 (a) | 397 |

-continued

| Example No. | Structure | Chemical Name | HPLC rt (min), method | Mass (M + H)+ m/z |
|---|---|---|---|---|
| 50 | 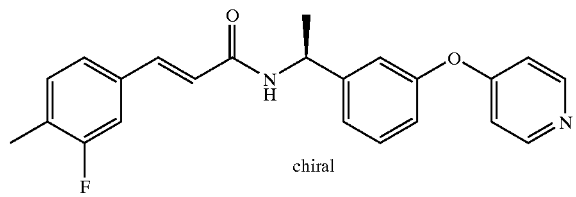 | (S)-3-(3-Fluoro-4-methyl-phenyl)-N-{1-[3-(pyridin-4-yl-oxy)-phenyl]-ethyl}-acryl-amide | 1.347 (a) | 377 |
| 51 | 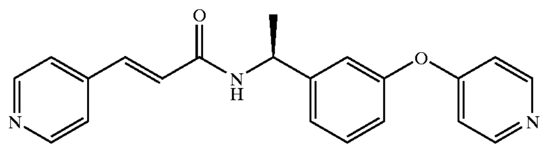 | (S)-3-Pyridin-4-yl-N-{1-[3-(pyridin-4-yloxy)-phenyl]-ethyl}-acrylamide | 0.633 (a) | 346 |
| 52 | 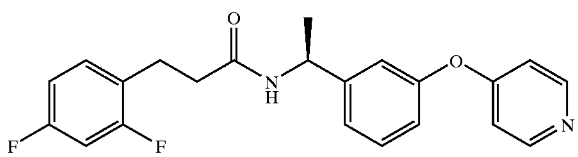 | (S)-3-(2,4-Difluoro-phenyl)-N-{1-[3-(pyridin-4-yloxy)-phenyl]-ethyl}-propion-amide | 1.197 (a) | 383 |
| 53 | 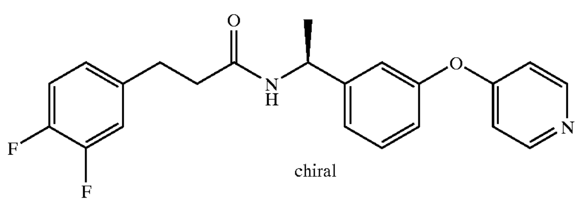 | (S)-3-(3,4-Difluoro-phenyl)-N-{1-[3-(pyridin-4-yloxy)-phenyl]-ethyl}-propion-amide | 1.180 (a) | 383 |

Example 54

(S)-3-phenyl-N-{1-[3-(pyrazine-2-yloxyl)-phenyl]-ethyl}-acrylamide

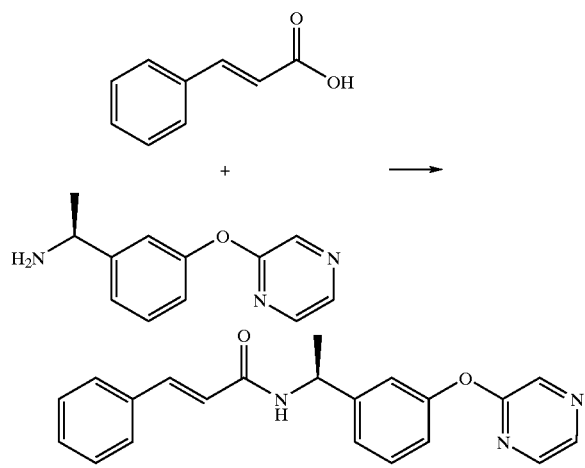

The title compound was prepared following the general procedues as described for Example 1 with the exception that (S)-1-[3-(pyrazin-2-yloxy)-phenyl]-ethylamine was used.

$^1$H NMR (CDCl$_3$, 300 MHz): δ 1.56 (d, J=6.9 Hz, 3H), 5.32 (m, 1H), 5.99 (d, J=7.5 Hz, 1H), 6.39 (d, J=15.6 Hz, 1H), 7.07 (d, J=7.9 Hz, 1H), 7.17 (s, 1H), 7.26 (m, 1H), 7.34 (m, 4H), 7.47(m, 2H), 7.63 (d, J=15.6 Hz, 1H), 8.09 (s, 1H), 8.26 (s, 1H), 8.41 (s, 1H).

$^{13}$C NMR (CDCl$_3$, 75 MHz): δ 21.4, 48.5, 119.2, 120.2, 120.6, 123.4, 127.8, 128.8, 129.7, 130.0, 134.8, 136.0, 138.6, 141.1, 141.4, 145.3, 153.4, 160.1, 165.0.

MS (M+H)$^+$346.

Examples 55–68

Examples 55–68 were made from the appropriate acids following the general procedures as described for Example 54.

| Example No. | Structure | Chemical Name | HPLC rt (min), method | Mass (M + H)+ m/z |
|---|---|---|---|---|
| 55 | 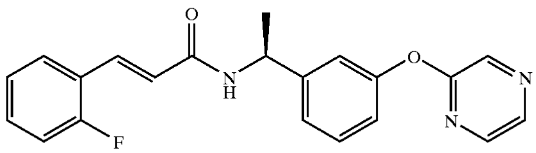 | (S)-3-(2-Fluoro-phenyl)-N-{1-[3-(pyrazin-2-yloxy)-phenyl]-ethyl}-acrylamide | 1.487 (b) | 364 |
| 56 | 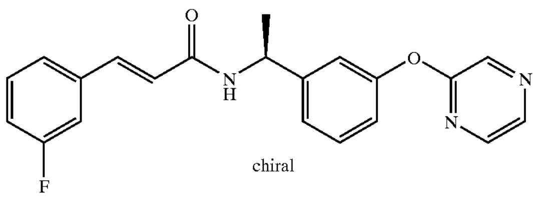 | (S)-3-(3-Fluoro-phenyl)-N-{1-[3-(pyrazin-2-yloxy)-phenyl]-ethyl}-acrylamide | 1.497 (b) | 364 |
| 57 | 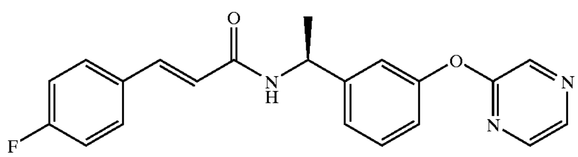 | (S)-3-(4-Fluoro-phenyl)-N-{1-[3-(pyrazin-2-yloxy)-phenyl]-ethyl}-acrylamide | 1.487 (a) | 364 |
| 58 | 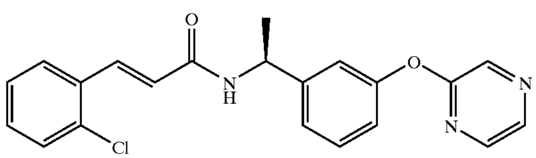 | (S)-3-(2-Chloro-phenyl)-N-{1-[3-(pyrazin-2-yloxy)-phenyl]-ethyl}-acrylamide | 1.560 (a) | 380 |
| 59 | 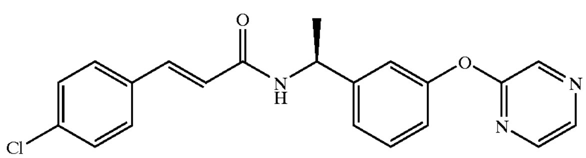 | (S)-3-(4-Chloro-phenyl)-N-{1-[3-(pyrazin-2-yloxy)-phenyl]-ethyl}-acrylamide | 1.603 (a) | 380 |
| 60 | 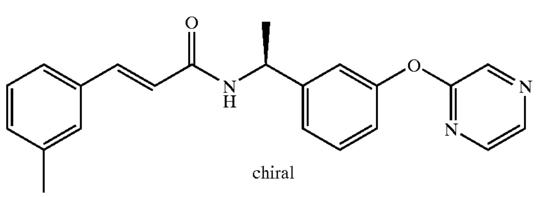 | (S)-N-{1-[3-(Pyrazin-2-yloxy)-phenyl]-ethyl}-3-m-tolyl-acrylamide | 1.553 (a) | 360 |
| 61 | 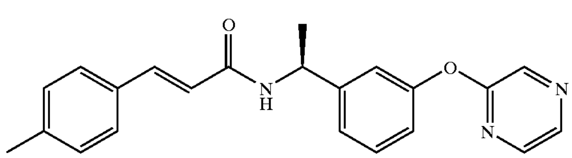 | (S)-N-{1-[3-(Pyrazin-2-yloxy)-phenyl]-ethyl}-3-p-tolyl-acrylamide | 1.573 (a) | 360 |

-continued

| Example No. | Structure | Chemical Name | HPLC rt (min), method | Mass (M + H)+ m/z |
|---|---|---|---|---|
| 62 | 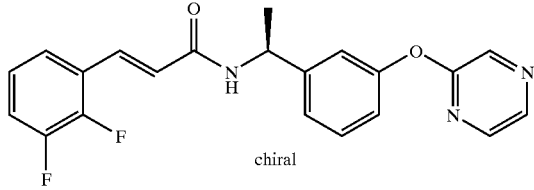 | (S)-3-(2,3-Difluoro-phenyl)-N-{1-[3-(pyrazin-2-yl-oxy)-phenyl]-ethyl}-acryl-amide | 1.540 (a) | 382 |
| 63 | 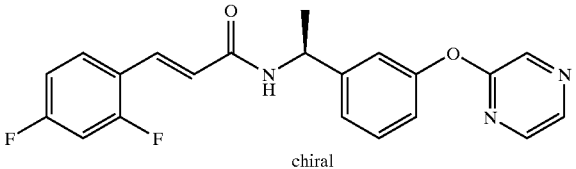 | (S)-3-(2,4-Difluoro-phenyl)-N-{1-[3-(pyrazin-2-yl-oxy)-phenyl]-ethyl}-acryl-amide | 1.527 (a) | 382 |
| 64 | 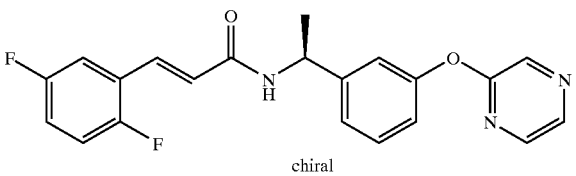 | (S)-3-(2,5-Difluoro-phenyl)-N-{1-[3-(pyrazin-2-yl-oxy)-phenyl]-ethyl}-acryl-amide | 1.510 (a) | 382 |
| 65 | 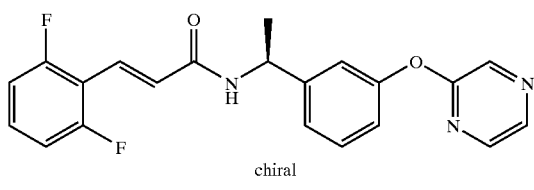 | (S)-3-(2,6-Difluoro-phenyl)-N-{1-[3-(pyrazin-2-yl-oxy)-phenyl]-ethyl}-acryl-amide | 1.507 (a) | 382 |
| 66 | 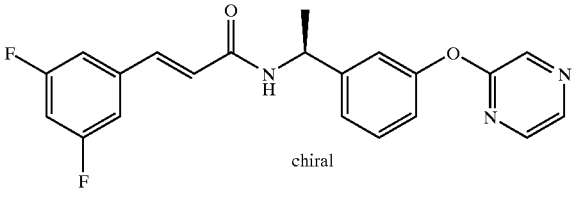 | (S)-3-(3,5-Difluoro-phenyl)-N-{1-[3-(pyrazin-2-yl-oxy)-phenyl]-ethyl}-acryl-amide | 1.550 (a) | 382 |
| 67 | 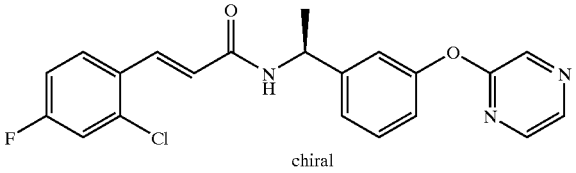 | (S)-3-(2-Chloro-4-fluoro-phenyl)-N-{1-[3-(pyrazin-2-yl-oxy)-phenyl]-ethyl}-acryl-amide | 1.637 (a) | 398 |
| 68 | 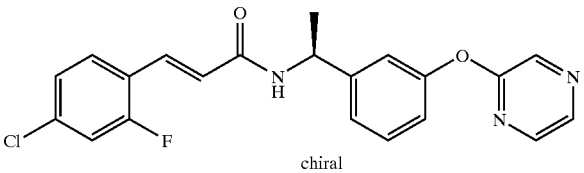 | (S)-3-(4-Chloro-2-fluoro-phenyl)-N-{1-[3-(pyrazin-2-yl-oxy)-phenyl]-ethyl}-acryl-amide | 1.670 (a) | 398 |

Example 69
(S)-3-(2-fluoro-phenyl)-N-{1-[3-(pyrimidin-2-yloxy)-phenyl]-ethyl}-acrylamide

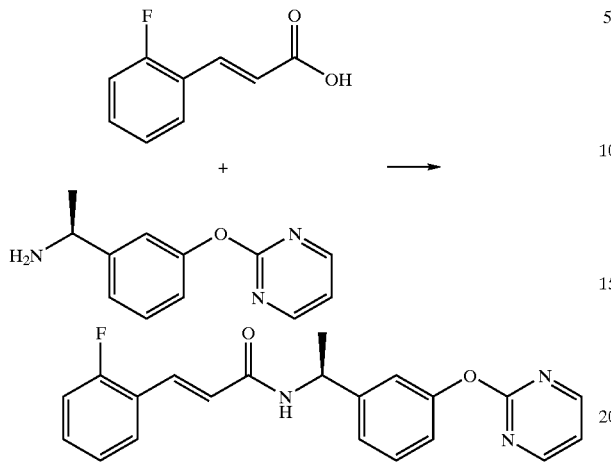

The title compound was prepared from 2-fluorocinnamic acid following the general procedures as described for Example 1 with the exception that (S)-1-[3-(pyrimidin-2-yloxy)-phenyl]-ethylamine was used.

$^1$H NMR (CDC$_3$, 300 MHz): δ 1.57 (d, J=6.9 Hz, 3H), 5.34 (m, 1H), 6.03 (d, J=7.7 Hz, 1H), 6.53 (d, J=15.8, 1H), 7.10 (m, 4H), 7.27 (m, 3H), 7.41 (m, 2H), 7.69 (d, J=15.8, 1H), 8.54 (d, J=4.8 Hz, 2H).
$^{13}$C NMR (CDCl$_3$, 75 MHz): δ 21.3, 48.5, 116.0, 116.3, 119.6, 120.7, 122.8, 123.0, 123.6, 123.7, 124.4, 129.7, 129.8, 131.0, 134.4, 144.9, 153.2, 159.7, 163.1, 164.8, 165.3.
MS: (M+H)$^+$364.

Examples 70–71

Examples 70–71 were made from the appropriate acids following the general procedures as described for Example 69.

Example 72
(S)-3-phenyl-N{1-[3-(pyrimidin-5-yloxy)-phenyl]-ethyl}-acrylamide

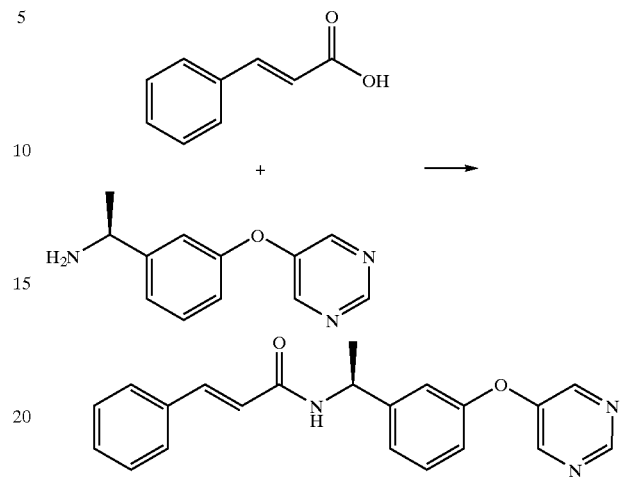

The title compound was prepared following the general procedures as described for Example 1 with the exception that (S)-1-[3-(pyrimidin-5-yloxy)-phenyl]-ethylamine was used.

$^1$H NMR (CDCl$_3$,300 MHz): δ 1.55 (d, J=6.9 Hz, 3H), 5.27 (m, 1H), 5.91 (d, J=7.3 Hz, 1H), 6.40 (d, J=15.8, 1H), 6.92 (m, 1H), 7.09 (s, 1H), 7.24 (m, 1H), 7.35 (m, 4H), 7.48 (m, 2H), 7.64 (d, J=15.8, 1H), 8.48 (s, 2H), 8.96 (s, 1H).
$^{13}$C NMR (CDCl$_3$, 75 MHz): δ 21.8, 48.6, 117.0, 117.6, 120.3, 122.8, 127.8, 128.8, 129.8, 130.6, 134.7, 141.7, 146.4, 147.1, 152.2, 153.3, 155.7, 165.0.
MS: (M+H)$^+$346.

Examples 73–83

Examples 73–83 were prepared from the appropriate acid following the general procedures as described for Example 72.

| Example No. | Structure | Chemical Name | HPLC rt (min), method | Mass (M + H)$^+$ m/z |
|---|---|---|---|---|
| 70 | (structure with 2,3-difluorophenyl, chiral) | (S)-3-(2,3-Difluoro-phenyl)-N-{1-[3-(pyrimidin-2-yloxy)-phenyl]-ethyl}-acrylamide | 1.593 (a) | 382 |
| 71 | (structure with 2,6-difluorophenyl, chiral) | (S)-3-(2,6-Difluoro-phenyl)-N-{1-[3-(pyrimidin-2-yloxy)-phenyl]-ethyl}-acrylamide | 1.563 (a) | 382 |

| Example No. | Structure | Chemical Name | HPLC rt (min), method | Mass (M + H)+ m/z |
|---|---|---|---|---|
| 73 | 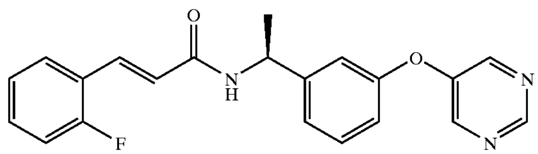 | (S)-3-(2-Fluoro-phenyl)-N-{1-[3-(pyrimidin-5-yl-oxy)-phenyl]-ethyl}-acryl-amide | 1.623 (a) | 364 |
| 74 | 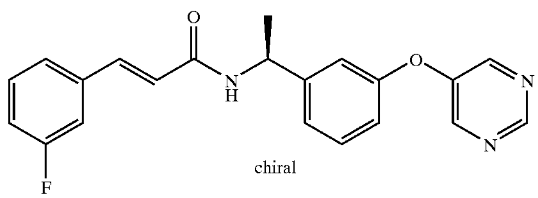 | (S)-3-(3-Fluoro-phenyl)-N-{1-[3-(pyrimidin-5-yloxy)-phenyl]-ethyl}-acryl-amide | 1.643 (a) | 364 |
| 75 | 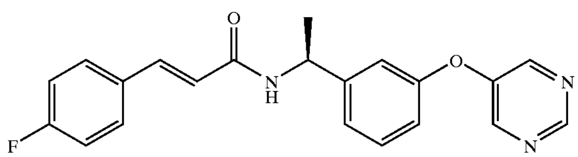 | (S)-3-(4-Fluoro-phenyl)-N-{1-[3-(pyrimidin-5-yl-oxy)-phenyl]-ethyl}-acryl-amide | 1.627 (a) | 364 |
| 76 | 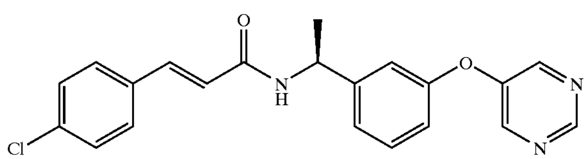 | (S)-3-(4-Chloro-phenyl)-N-{1-[3-(pyrimidin-5-yl-oxy)-phenyl]-ethyl}-acryl-amide | 1.757 (a) | 380 |
| 77 | 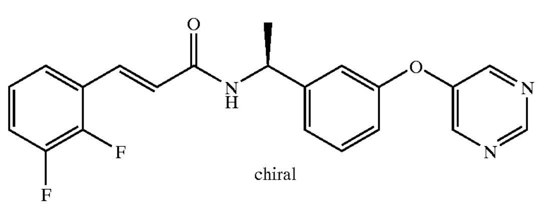 | (S)-3-(2,3-Difluoro-phenyl)-N-{1-[3-(pyrimidin-5-yloxy)-phenyl]-ethyl}-acrylamide | 1.673 (a) | 382 |
| 78 | 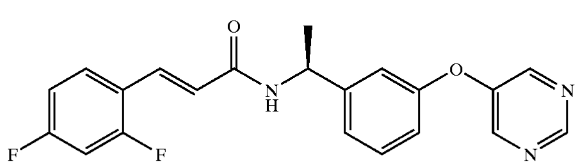 | (S)-3-(2,4-Difluoro-phenyl)-N-{1-[3-(pyrimidin-5-yloxy)-phenyl]-ethyl}-acrylamide | 1.663 (a) | 382 |
| 79 | 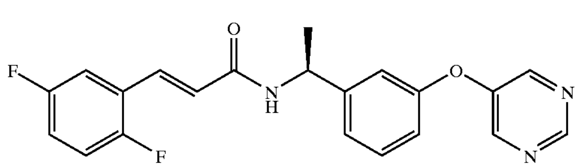 | (S)-3-(2,5-Difluoro-phenyl)-N-{1-[3-(pyrimidin-5-yloxy)-phenyl]-ethyl}-acrylamide | 1.653 (a) | 382 |

-continued

| Example No. | Structure | Chemical Name | HPLC rt (min), method | Mass (M + H)+ m/z |
|---|---|---|---|---|
| 80 | 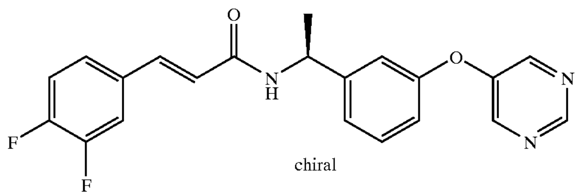 | (S)-3-(3,4-Difluoro-phenyl)-N-{1-[3-(pyrimidin-5-yloxy)-phenyl]-ethyl}-acrylamide | 1.670 (a) | 382 |
| 81 | 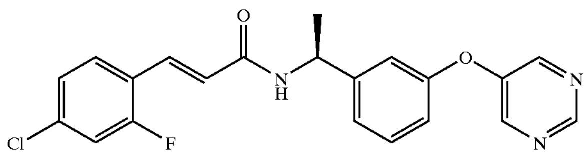 | (S)-3-(4-Chloro-2-fluoro-phenyl)-N-{1-[3-(pyrimidin-5-yloxy)-phenyl]-ethyl}-acrylamide | 1.803 (a) | 398 |
| 82 | 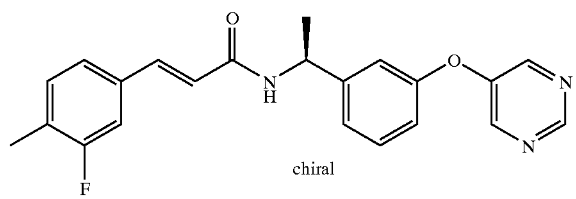 | (S)-3-(3-Fluoro-4-methyl-phenyl)-N-{1-[3-(pyrimidin-5-yloxy)-phenyl]-ethyl}-acrylamide | 1.760 (a) | 378 |
| 83 | 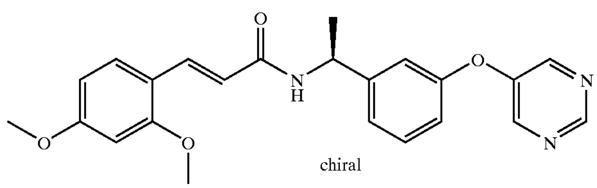 | (S)-3-(2,4-Dimethoxy-phenyl)-N-{1-[3-(pyrimidin-5-yloxy)-phenyl]-ethyl}-acrylamide | 1.647 (a) | 406 |

Example 84

(S)-3-(3-Chloro-phenyl)-N-(1-{3-[(pyridin-3-ylmethyl)-amino]-phenyl}-ethyl)-acrylamide

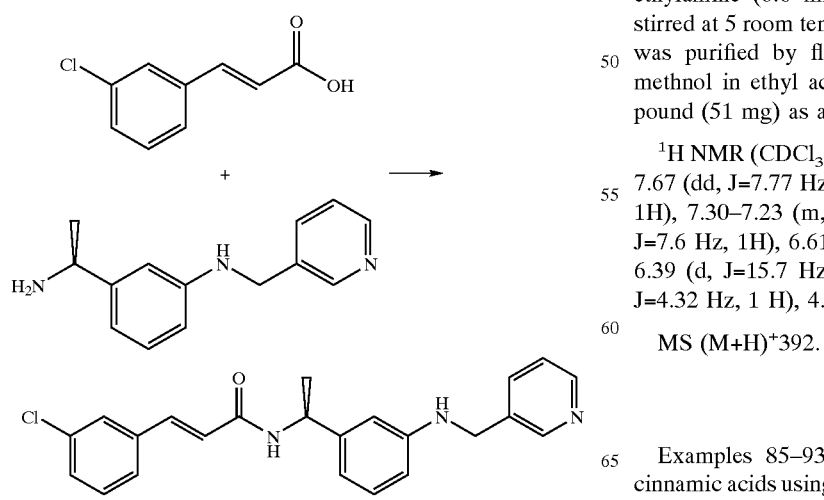

A mixture of (s)-[3-(1-amino-ethyl)-phenyl]-pyridin-3-ylmethyl-amine (0.2 mmol), 3-chlorocinnamic acid (0.2 mmol), EDACeHCl (0.4 mmol), DMAP (0.2 mmol), triethylamine (0.6 mmol) in dichloromethane (4 mL) was stirred at room temperature for 12 h. The reaction mixture was purified by flash chromatography eluting with 5% methnol in ethyl acetate to provide the desired title compound (51 mg) as a solid.

$^1$H NMR (CDCl$_3$): δ 8.58 (s, 1H), 8.53 (d, J=3.9 Hz, 1H), 7.67 (dd, J=7.77 Hz, 1H), 7.54 (d, J=15.7 Hz, 1H), 7.42 (s, 1H), 7.30–7.23 (m, 3H), 7.16 (t, J=7.8 Hz, 1H), 6.72 (d, J=7.6 Hz, 1H), 6.61 (s, 1H), 6.51 (dd, J=7.7, 2.1 Hz, 1H), 6.39 (d, J=15.7 Hz, 1H), 6.20 (d, J=8 Hz, 1H), 5.17 (d, J=4.32 Hz, 1 H), 4.32 (s, 2H), 1.50 (d, J=6.9 Hz, 3H).

MS (M+H)$^+$392.

Examples 85–93

Examples 85–93 were prepared from the appropriate cinnamic acids using the general procedures as described for Example 84.

| Example No. | Structure | Chemical Name | HPLC rt (min), method | Mass (M + H)+ m/z |
|---|---|---|---|---|
| 85 | 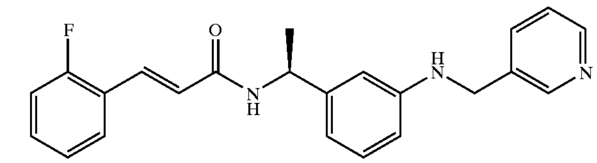 | (S)-N-[1-(3-Pyridin-3-ylmethyl-amino-phenyl)-ethyl]-3-(2-fluoro-phenyl)-acrylamide | 1.101 (c) | 376 |
| 86 | 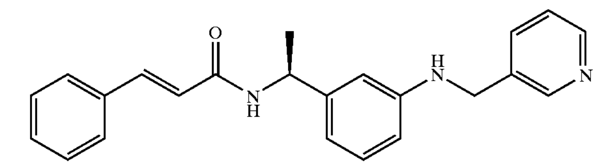 | (S)-N-[1-(3-Pyridin-3-ylmethyl-amino-phenyl)-ethyl]-3-phenyl-acrylamide | 0.99 (c) | 358 |
| 87 | 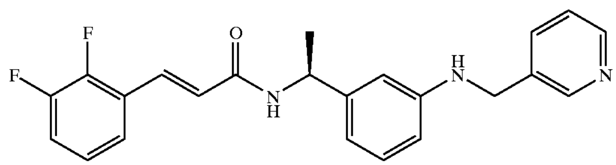 | (S)-N-[1-(3-Pyridin-3-ylmethyl-amino-phenyl)-ethyl]-3-(2,3-difluoro-phenyl)-acrylamide | 1.06 (c) | 394 |
| 88 | 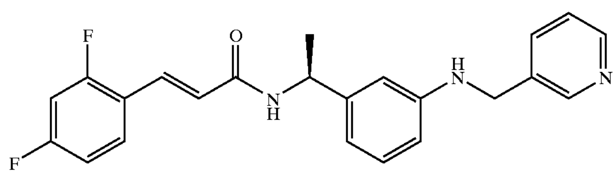 | (S)-N-[1-(3-Pyridin-3-ylmethyl-amino-phenyl)-ethyl]-3-(2,4-difluoro-phenyl)-acrylamide | 1.03 (c) | 394 |
| 89 | 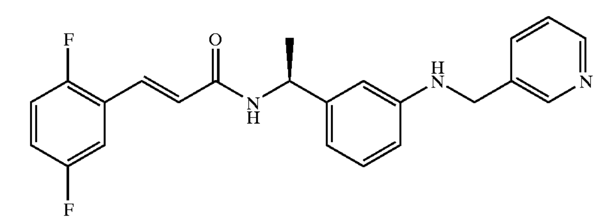 | (S)-N-[1-(3-Pyridin-3-ylmethyl-amino-phenyl)-ethyl]-3-(2,5-difluoro-phenyl)-acrylamide | 1.03 (c) | 394 |
| 90 | 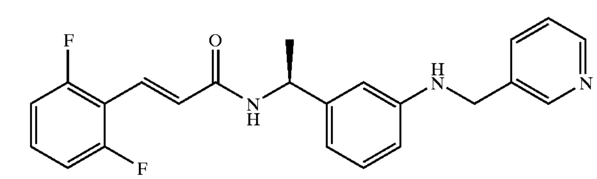 | (S)-N-[1-(3-Pyridin-3-ylmethyl-amino-phenyl)-ethyl]-3-(2,6-difluoro-phenyl)-acrylamide | 1.02 (c) | 394 |
| 91 | 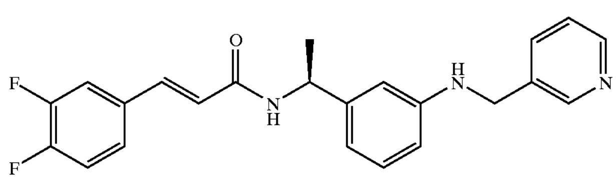 | (S)-N-[1-(3-Pyridin-3-ylmethyl-amino-phenyl)-ethyl]-3-(3,4-difluoro-phenyl)-acrylamide | 1.06 (c) | 394 |
| 92 | 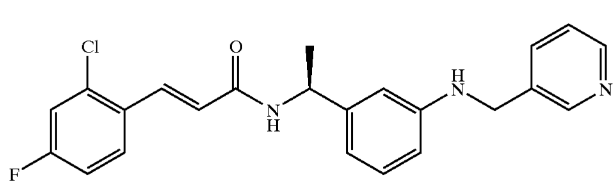 | (S)-N-[1-(3-Pyridin-3-ylmethyl-amino-phenyl)-ethyl]-3-(2-chloro-4-fluoro-phenyl)-acrylamide | 1.13 (c) | 410 |

| Example No. | Structure | Chemical Name | HPLC rt (min), method | Mass (M + H)+ m/z |
|---|---|---|---|---|
| 93 | 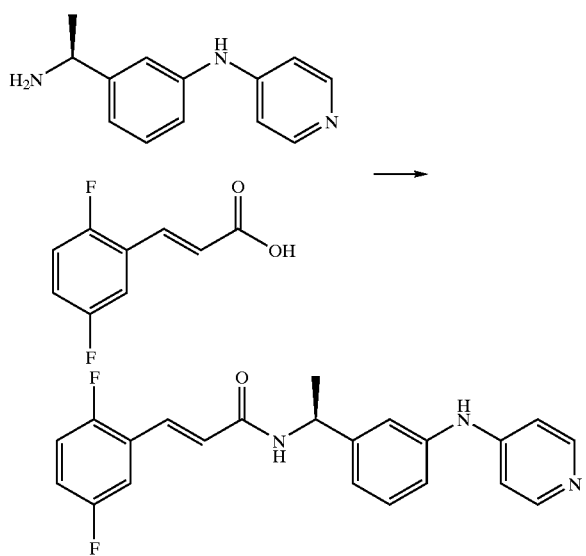 | (S)-N-[1-(3-Pyridin-3-ylmethyl-amino-phenyl)-eth-yl]-3-(4-chloro-2-fluoro-phenyl)-acrylamide | 1.11 (c) | 410 |

Example 94

(S)-[3-(2,5-Difluoro-phenyl)-N-{1-[3-(pyridin-4-ylamino)-phenyl]ethyl}-acrylamide

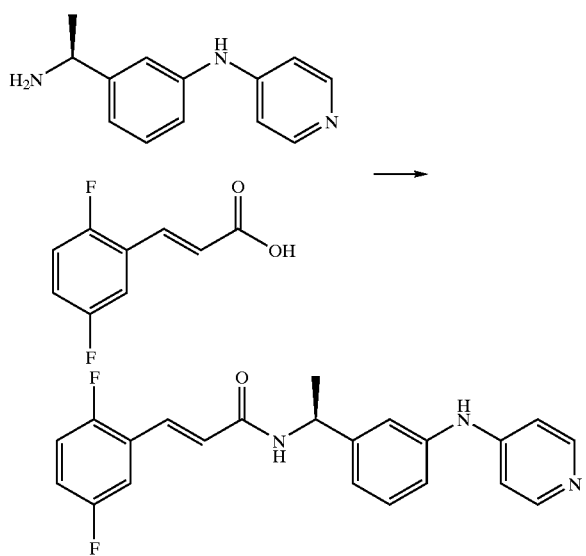

A mixture of (S)-[3-(1-amino-ethyl)-phenyl]-pyridin-4-yl-amine (0.1 mmol), 2.5-difluoro-chlorocinnamic acid (0.1 mmol), EDAC.HCl (0.2 mmol), DMAP (0.1 mmol), triethylamine (0.3 mmol) in dichloromethane (2 mL) was stirred at room temperature overnight. The reaction mixture was purified by flash chromatography with 5% methnol in ethyl acetate to provide the title compound (31 mg) as a solid.

MS (M+H)+380.

What is claimed is:

1. A compound of Formula I or a pharmaceutically acceptable salt thereof

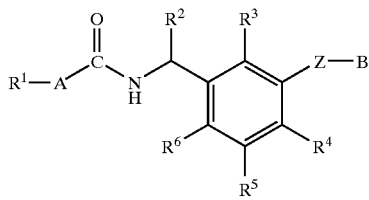

wherein $R^1$ is selected from the group consisting of pyridinyl, 3-quinolinyl, thienyl, furanyl, $C_{3-6}$ cycloalkyl and phenyl optionally substituted with substituent independently selected from the group consisting of halogen, $C_{1-4}$ alkyl, $C_{1-4}$ alkoxy, trifluoromethyl, trifluoromethoxy and nitro;

A is —CH=CH— or $CH_2)_n$—;

$R^2$ is $C_{1-4}$ alkyl, $CF_3$ or hydroxymethyl;

$R^3$, $R^4$, $R^5$ and $R^6$ each are independently hydrogen or fluoro;

Z is oxygen or —$NR^7(CH_2)_m$—;

n is an integer of 0, 1, 2 or 3;

m is an integer of 0 or 1;

$R^7$ is hydrogen or $C_{1-4}$ alkyl; and

B is pyridinyl, pyrimidinyl or pyrazinyl optionally substituted with a subsituent selected from the group consisting of $C_{1-4}$ alkyl, halogen, $C_{1-4}$ alkoxy and trifluoromethyl.

2. The compound of claim 1 having the Formula Ic or a pharmaceutically acceptable salt thereof

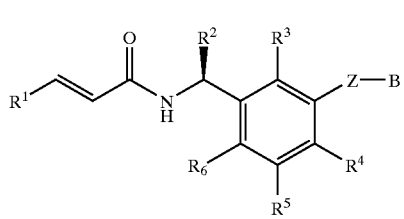

wherein $R^1$ is selected from the group consisting of pyridinyl, 3-quinolinyl, thienyl, furanyl, $C_{3-6}$ cycloalkyl and phenyl optionally substituted with substituent independently selected from the group consisting of halogen, $C_{1-4}$ alkyl, $C_{1-4}$ alkoxy, trifluoromethyl, trifluoromethoxy and nitro;

$R^2$ is methyl or hydroxymethyl;

$R^3$, $R^4$, $R^5$ and $R^6$ each are independently hydrogen or fluoro;

Z is oxygen or —$NR^7(CH_2)_m$—;

n is an integer of 0, 1, 2 or 3;

m is an integer of 0 or 1;

$R^7$ is hydrogen or $C_{1-4}$ alkyl; and

B is pyridinyl, pyrimidinyl or pyrazinyl optionally substituted with a subsituent selected from the group consisting of $C_{1-4}$ alkyl, halogen, $C_{1-4}$ alkoxy and trifluoromethyl.

3. The compound of claim 1 selected from the group consisting of:

(S)-3-(2-fluoro-phenyl)-N-{1-[3-(pyridin-2-yloxy)-phenyl]-ethyl}-acrylamide;

(S)-3-(3-fluoro-phenyl)-N-{1-[3-(pyridin-2-yloxy)-phenyl]-ethyl}-acrylamide;
(S)-3-(4-fluoro-phenyl)-N-{1-[3-(pyridin-2-yloxy)-phenyl]-ethyl}-acrylamide;
(S)-3-(2,3-difluoro-phenyl)-N-{1-[3-(pyridin-2-yloxy)-phenyl]-ethyl}-acrylamide;
(S)-3-(2,4-difluoro-phenyl)-N-{1-[3-(pyridin-2-yloxy)-phenyl]-ethyl}-acrylamide;
(S)-3-(2,5-difluoro-phenyl)-N-{1-[3-(pyridin-2-yloxy)-phenyl]-ethyl}-acrylamide;
(S)-3-(2,6-difluoro-phenyl)-N-{1-[3-(pyridin-2-yloxy)-phenyl]-ethyl}-acrylamide;
(S)-3-(3,4-difluoro-phenyl)-N-{1-[3-(pyridin-2-yloxy)-phenyl]-ethyl}-acrylamide;
(S)-3-(3,5-difluoro-phenyl)-N-{1-[3-(pyridin-2-yloxy)-phenyl]-ethyl}-acrylamide;
(S)-3-(2-fluoro-phenyl)-N-{1-[3-(pyridin-3-yloxy)-phenyl]-ethyl}-acrylamide;
(S)-3-(3-fluoro-phenyl)-N-{1-[3-(pyridin-3-yloxy)-phenyl]-ethyl}-acrylamide;
(S)-3-(4-fluoro-phenyl)-N-{1-[3-(pyridin-3-yloxy)-phenyl]-ethyl}-acrylamide;
(S)-3-(2,3-difluoro-phenyl)-N-{1-[3-(pyridin-3-yloxy)-phenyl]-ethyl}-acrylamide
(S)-3-(2,4-difluoro-phenyl)-N-{1-[3-(pyridin-3-yloxy)-phenyl]-ethyl}-acrylamide;
(S)-3-(2,5-difluoro-phenyl)-N-{1-[3-(pyridin-3-yloxy)-phenyl]-ethyl}-acrylamide;
(S)-3-(3,4-difluoro-phenyl)-N-{1-[3-(pyridin-3-yloxy)-phenyl]-ethyl}-acrylamide;
(S)-3-(4-fluoro-phenyl)-N-{1-[3-(6-methyl-pyridin-3-yloxy)-phenyl]-ethyl}-acrylamide;
(S)-3-(2,4-difluoro-phenyl)-N-{1-[3-(6-methyl-pyridin-3-yloxy)-phenyl]-ethyl}-acrylamide;
(S)-3-(2,5-difluoro-phenyl)-N-{1-[3-(6-methyl-pyridin-3-yloxy)-phenyl]-ethyl}-acrylamide;
(S)-N-{1-[3-(6-methyl-pyridin-3-yloxy)-phenyl]-ethyl}-3-(2,4,5-trifluoro-phenyl)-acrylamide;
(S)-3-(2-fluoro-phenyl)-N-{1-[3-(pyridin-4-yloxy)-phenyl]-ethyl}-acrylamide;
(S)-3-(3-fluoro-phenyl)-N-{1-[3-(pyridin-4-yloxy)-phenyl]-ethyl}-acrylamide;
(S)-3-(4-fluoro-phenyl)-N-{1-[3-(pyridin-4-yloxy)-phenyl]-ethyl}-acrylamide;
(S)-3-(2,3-difluoro-phenyl)-N-{1-[3-(pyridin-4-yloxy)-phenyl]-ethyl}-acrylamide;
(S)-3-(2,4-difluoro-phenyl)-N-{1-[3-(pyridin-4-yloxy)-phenyl]-ethyl}-acrylamide;
(S)-3-(2,6-difluoro-phenyl)-N-{1-[3-(pyridin-4-yloxy)-phenyl]-ethyl}-acrylamide;
(S)-3-(2,5-difluoro-phenyl)-N-{1-[3-(pyridin-4-yloxy)-phenyl]-ethyl}-acrylamide;
(S)-3-(3,4-difluoro-phenyl)-N-{1-[3-(pyridin-4-yloxy)-phenyl]-ethyl}-acrylamide;
(S)-3-(3,5-difluoro-phenyl)-N-{1-[3-(pyridin-4-yloxy)-phenyl]-ethyl}-acrylamide;
(S)-3-(2,4-difluoro-phenyl)-N-{1-[3-(pyridin-4-yloxy)-phenyl]-ethyl}-propionamide;
(S)-3-(3,4-difluoro-phenyl)-N-{1-[3-(pyridin-4-yloxy)-phenyl]-ethyl}-propionamide;
(S)-3-(2-fluoro-phenyl)-N-{1-[3-(pyrazin-2-yloxy)-phenyl]-ethyl}-acrylamide;
(S)-3-(3-fluoro-phenyl)-N-{1-[3-(pyrazin-2-yloxy)-phenyl]-ethyl}-acrylamide;
(S)-3-(4-fluoro-phenyl)-N-{1-[3-(pyrazin-2-yloxy)-phenyl]-ethyl}-acrylamide;
(S)-3-(2,3-difluoro-phenyl)-N-{1-[3-(pyrazin-2-yloxy)-phenyl]-ethyl}-acrylamide;
(S)-3-(2,4-difluoro-phenyl)-N-{1-[3-(pyrazin-2-yloxy)-phenyl]-ethyl}-acrylamide;
(S)-3-(2,6-difluoro-phenyl)-N-{1-[3-(pyrazin-2-yloxy)-phenyl]-ethyl}-acrylamide;
(S)-3-(3,5-difluoro-phenyl)-N-{1-[3-(pyrazin-2-yloxy)-phenyl]-ethyl}-acrylamide;
(S)-3-(2,3-difluoro-phenyl)-N-{1-[3-(pyrimidin-2-yloxy)-phenyl]-ethyl}-acrylamide;
(S)-3-(2,6-difluoro-phenyl)-N-{1-[3-(pyrimidin-2-yloxy)-phenyl]-ethyl}-acrylamide;
(S)-3-(2-fluoro-phenyl)-N-{1-[3-(pyrimidin-5-yloxy)-phenyl]-ethyl}-acrylamide;
(S)-3-(3-fluoro-phenyl)-N-{1-[3-(pyrimidin-5-yloxy)-phenyl]-ethyl}-acrylamide;
(S)-3-(4-fluoro-phenyl)-N-{1-[3-(pyrimidin-5-yloxy)-phenyl]-ethyl}-acrylamide;
(S)-3-(2,4-difluoro-phenyl)-N-{1-[3-(pyrimidin-5-yloxy)-phenyl]-ethyl}-acrylamide;
(S)-N-[1-(3-pyridin-3-ylmethylamino-phenyl)-ethyl]-3-(2-fluoro-phenyl)-acrylamide;
(S)-N-[1-(3-pyridin-3-ylmethylamino-phenyl)-ethyl]-3-phenyl-acrylamide;
(S)-N-[1-(3-pyridin-3-ylmethylamino-phenyl)-ethyl]-3-(2,4-difluoro-phenly)-acrylamide; and
(S)-N-[1-(3-pyridin-3-ylmethylamino-phenyl)-ethyl]-3-(2,6-difluoro-phenyl)-acrylamide;

or a pharmaceutically acceptable salt thereof.

4. A pharmaceutical composition comprising a therapeutically effective amount of the compound of claim 1 in association with a pharmaceutically acceptable carrier, adjuvant or diluent.

5. a method of for the treatment of disorders responsive to opening of the KCNQ potassium channels in a mammal in need thereof, wherein said disorders are acute and chronic pain, migraine, neuropathic pain, bipolar disorders, convulsions, mania, epilepsy, anxiety, and depression, which comprises administer to said mammal a therapeutically effective amount of the compound of claim 1.

6. The method of claim 5 wherein said disorder is migraine.

7. The method of claim 6 wherein said disorder is neuropathic pain.

* * * * *